(12) United States Patent
Sadowski et al.

(10) Patent No.: US 7,776,015 B2
(45) Date of Patent: Aug. 17, 2010

(54) NEEDLE ASSISTED JET INJECTOR

(75) Inventors: Peter L. Sadowski, Woodbury, MN (US); David M. Deboer, Brighton, MI (US); Claude L. Berman, Ypsilanti, MI (US); Paul R. Lesch, Jr., Lexington, MI (US); Margaret L. Holland, Rochester, NY (US)

(73) Assignee: Antares Pharma Inc., Minneapolis, MN (US)

( * ) Notice: Subject to any disclaimer, the term of this patent is extended or adjusted under 35 U.S.C. 154(b) by 0 days.

(21) Appl. No.: 11/002,687

(22) Filed: Dec. 3, 2004

(65) Prior Publication Data

US 2005/0080377 A1    Apr. 14, 2005

Related U.S. Application Data

(60) Division of application No. 10/861,429, filed on Jun. 7, 2004, which is a division of application No. 09/779,603, filed on Feb. 9, 2001, now Pat. No. 6,746,429, which is a continuation of application No. PCT/US99/17946, filed on Aug. 10, 1999.

(60) Provisional application No. 60/096,464, filed on Aug. 11, 1998.

(51) Int. Cl.
  *A61M 37/00* (2006.01)
(52) U.S. Cl. ............... 604/131; 604/68; 604/133
(58) Field of Classification Search ............ 604/131, 604/68, 137, 143, 201, 198, 202, 206, 187, 604/188; 141/329
See application file for complete search history.

(56) References Cited

U.S. PATENT DOCUMENTS

| 4,222,392 A | * | 9/1980 | Brennan | 600/556 |
| 4,378,015 A | | 3/1983 | Wardlaw | 128/218 F |
| 4,553,962 A | | 11/1985 | Brunet | 604/198 |
| 4,790,824 A | | 12/1988 | Morrow et al. | 604/143 |

(Continued)

FOREIGN PATENT DOCUMENTS

WO    WO 95/29720    11/1995

(Continued)

OTHER PUBLICATIONS

Hingson, Robert A. et al., "Clinical Studies with Jet Injection, A New Method of Drug Administration", Current Researchers in Anesthesia and Analgesia, Official Organ of the International Anesthesia Research Society, vol. 26, No. 6, pp. 221-230, (1947).

(Continued)

*Primary Examiner*—Kevin C Sirmons
*Assistant Examiner*—Phillip Gray
(74) *Attorney, Agent, or Firm*—Dorsey & Whitney LLP

(57) ABSTRACT

A jet injection device with a fluid chamber in a housing member for holding about 0.02 ml to about 3 ml of a medicament. An injection-assisting needle has an injection end that extends from the housing for inserting into a patient to a depth of up to about 5 mm. A force-generating source is configured to apply a pressure reaching about 100-1000 psi to the medicament in the chamber to expel the medicament through the injecting end of the needle.

22 Claims, 26 Drawing Sheets

U.S. PATENT DOCUMENTS

| | | | |
|---|---|---|---|
| 4,929,238 A * | 5/1990 | Baum | 604/208 |
| 5,062,830 A | 11/1991 | Dunlap | 604/68 |
| 5,176,643 A * | 1/1993 | Kramer et al. | 604/135 |
| 5,304,128 A * | 4/1994 | Haber et al. | 604/68 |
| 5,599,302 A | 2/1997 | Lilley et al. | 604/68 |
| 5,769,138 A | 6/1998 | Sadowski et al. | 141/329 |
| 6,056,716 A | 5/2000 | D'Antonio et al. | 604/68 |

FOREIGN PATENT DOCUMENTS

| | | |
|---|---|---|
| WO | WO 97/14455 | 4/1997 |
| WO | WO 99/03521 | 1/1999 |
| WO | WO 99/22790 | 5/1999 |

OTHER PUBLICATIONS

Hingson, Robert A. et al., "A Survey of the Development of Jet Injection in Parenteral Therapy", Current Researchers in Anesthesia and Analgesia, Official Organ of the International Anesthesia Research Society, vol. 31, No. 6. pp. 361-366 (1952).

* cited by examiner

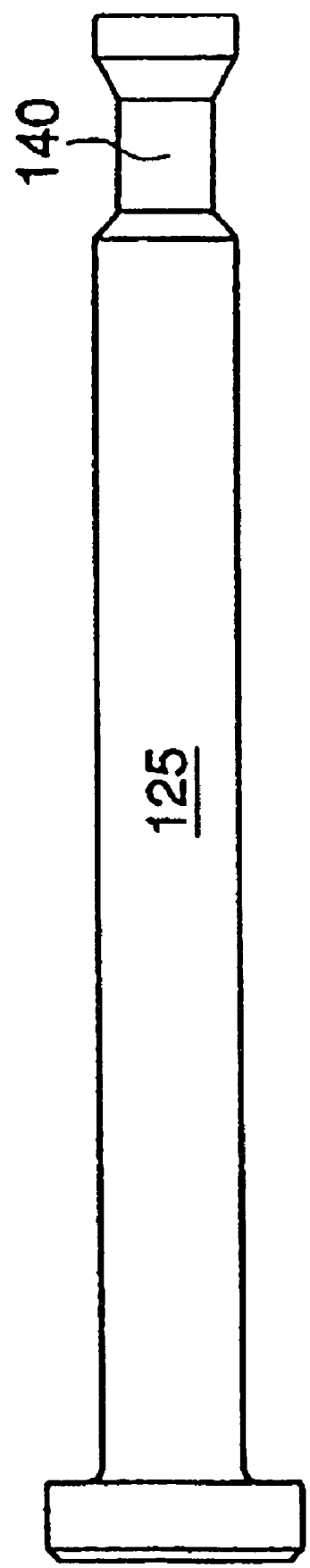

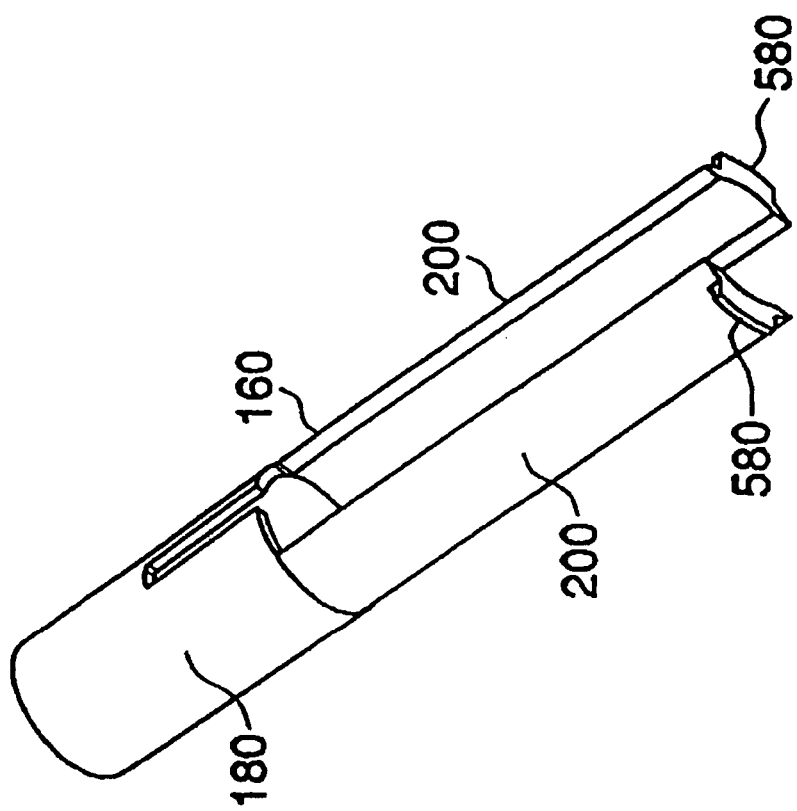

NEEDLE ASSISTED JET INJECTOR

CROSS-REFERENCE TO RELATED APPLICATIONS

This application is a division of U.S. application Ser. No. 10/861,429, filed Jun. 7, 2004, which is a division of U.S. application Ser. No. 09/779,603, filed Feb. 9, 2001, now U.S. Pat. No. 6,746,429, which is a continuation of International Patent Application No. PCT/US99/17946, filed Aug. 10, 1999, which claims priority to U.S. Provisional Application No. 60/096,464, filed on Aug. 11, 1998. The entire content of these applications is expressly incorporated herein by reference thereto.

FIELD OF THE INVENTION

The present invention is directed to a device for delivery of medicament, and in particular to a jet injector with a short needle to reduce the pressure at which the jet injector must eject the medicament for proper delivery.

BACKGROUND OF THE INVENTION

A wide variety of needleless injectors are known in the art. Examples of such injectors include those described in U.S. Pat. No. 5,599,302 issued to Lilley et al., U.S. Pat. No. 5,062,830 to Dunlap, and U.S. Pat. No. 4,790,824 to Morrow et al. In general, these and similar injectors administer medication as a fine, high velocity jet delivered under sufficient pressure to enable the jet to pass through the skin.

As the skin is a tissue composed of several layers and the injector is applied to the external surface of the outermost layer, the delivery pressure must be high enough to penetrate all layers of the skin. The layers of skin include the epidermis, the outermost layer of skin, the dermis, and the subcutaneous region. The required delivery pressure is typically greater than approximately 4000 p.s.i. (27,579 kPa) (measured as the force of the fluid stream divided by the cross-sectional area of the fluid stream).

Although this pressure is readily achievable with most injectors, there are some circumstances in which delivery of medicament to the subcutaneous region under a reduced pressure is desirable. For example, drugs that require a specific molecular structural arrangement, such as a linear protein configuration, may be rendered ineffective due to shear forces caused by the delivery of the drug at high pressures that alter the structural arrangement of the drug. As it is more difficult to deliver a large volume of fluid at a high pressure compared to a small volume, using a lower pressure facilitates delivery of a larger volume of fluid. Furthermore, the lower pressure could make manufacturing an injector device less expensive. The lower pressure would also reduce adverse stresses on the device and result in a corresponding increased useable device lifetime. Moreover, the lower pressure would make jet injection compatible with medicament stored and delivered in glass ampules, which typically cannot withstand the pressure typically reached by jet injectors.

One of the advantages associated with jet injectors is the absence of a hypodermic needle. Given the aversion to needles possessed by some, the absence of a needle provides a psychological benefit. Even devices that utilize conventional hypodermic needles have attempted to capitalize on this psychological benefit. For example, self-injectors or auto-injectors like the ones disclosed in U.S. Pat. Nos. 4,553,962, 4,378,015 and PCT International Publication numbers WO 95/29720, WO 97/14455 have retractable needles which are hidden until activation. Upon activation, the needle extends from the bottom of the device and penetrates the user's skin to deliver medicament. As none of these devices involves delivery of the medicament using jet injection, the medicament delivery location is limited by the length of the needle. For example, if delivery in the subcutaneous region is desired, the needle must be long enough to reach the subcutaneous region. Furthermore, as auto-injectors operate like syringes, the injection time is several seconds or longer. In contrast, jet injectors typically inject in fractions of a second.

U.S. Pat. No. 5,304,128 to Haber et al. describes a jet injecting syringe that uses a short needle to assist injection. The syringe uses a gas powered driven plunger to force medication through the syringe and out of the needle. The needle is retracted until the syringe is activated and then is extended to puncture the skin of the person injected. However, the needle remains extended after the syringe is used. The extended needle could lead to potential biohazards and safety concerns, such as accidental injections and spreading of diseases. Also, the gas powered plunger is both complicated and expensive to manufacture.

PCT Publication No. WO 99/03521 of Novo Nordisk discloses an undefined concept of "jet" injection. However, this publication does not teach one the details of the driving mechanism necessary to practice the concept.

PCT Publication No. WO 99/22790 of Elan Corporation teaches a needle assisted injector having a retractable shield that conceals the needle both before and after use of the injector. The disclosed injector has a driving mechanism that operates on pressure created by a chemical reaction. Because of this chemically operated driving mechanism, the injecting time for the injector is at least three seconds and more likely greater than five seconds. This relatively long injection time may create discomfort in the patient receiving the injection. Also, the needle may move during the lengthy injection and add to the patients discomfort.

Even with minimally invasive medical procedures, it is advantageous to maintain the time for the procedures at a minimum. Thus, there exists a need for a needle assisted jet injector that operates at relatively low pressure and that is capable of quickly delivering medicament. There also exists a need for such an injector having a retractable or concealed needle to prevent the medical hazards associated with exposed needles.

SUMMARY OF THE INVENTION

The present invention relates to a needle assisted jet injector. In one embodiment, the injection device includes a housing; a retractable injection-assisting needle at a distal end of the injector; a nozzle assembly defining a fluid chamber having an opening for slidingly receiving at least a portion of the needle and being removably associated with the housing; a plunger movable in the fluid chamber; a trigger assembly; and a force generating source operatively associated with the trigger assembly so that movement of the trigger assembly activates the energy source to move the plunger in a first direction to expel a fluid from the fluid chamber. The retractable injection-assisting needle has a needle tip located at a distal end of the needle with at least a portion configured and dimensioned to slide through the nozzle assembly opening; a discharge channel within the needle tip and terminating in an orifice through which the fluid is expelled; a body portion to direct fluid towards the discharge channel; a plunger receptor configured and dimensioned to receive at least a portion of the plunger; and a retraction element operatively associated with the needle and disposed substantially within the nozzle assembly. The needle is located within the nozzle assembly in a retracted position prior to activation of the force generating source. Movement of the plunger in the first direction upon activation of the energy source results in at least a portion of the needle tip extending beyond the nozzle assembly opening to a needle insertion point and expelling the fluid through the needle tip and past the needle insertion point to a needle injection site. The needle insertion point is located at the needle tip, and the needle injection site is distal to the needle tip. The retraction element returns the needle tip to the retracted position after activation of the energy source.

The retraction element may be a resilient O-ring, a spring, or a flexible membrane which moves to allow extension of the needle tip beyond the nozzle assembly opening and then returns to its original position to return the needle tip to its retracted position. The needle body can have an exterior surface which includes a ridge or recess for accommodating the retraction element. A shoulder can be disposed between the needle tip and the needle body for accommodating the retraction element. Preferably, the needle tip, when extended, has a length of approximately 1-5 mm.

In a preferred embodiment, the jet injector includes a housing having distal and proximal ends; a fluid chamber having a seal at one end and located within the housing for holding at least about 0.02 ml to 3 ml of a medicament; an injection-assisting needle having an injecting end and a piercing end and coupled to the distal end of the housing; a plunger movable within the fluid chamber; a force generating source capable of providing sufficient force on the plunger to eject an amount up to about 3 ml of the medicament from the fluid chamber in less than 2.75 seconds; a needle guard located at the distal end of the housing for concealing the needle, the needle guard being moveable between a protecting position and an injecting position; and an activation element operatively associated with the needle guard. The needle is moveable between a medicament storing position and a medicament delivering position. When the needle is in the medicament storing position, it is isolated from the fluid chamber. When the needle is in the medicament delivering position, the piercing end punctures the seal to provide a fluid pathway from the fluid chamber through the needle. Retraction of the needle guard exposes the injecting end of the needle to an insertion point and activation of the force generating source moves the plunger to expel medicament from the fluid chamber and thereby eject the amount of the medicament through the injecting end of the needle and past the needle insertion point to an injection site in less than 2.75 seconds. The needle insertion point is located at the injecting end of the needle, and the injection site is distal to the injecting end of the needle.

Retraction of the needle guard from the protecting position to the injecting position may activate the force generating source, which provides sufficient force to eject an amount of about 1 to 2 ml of the medicament in less than about 2.5 seconds. The jet injector can also include a locking element associated with the needle guard for locking the needle guard in the protecting position after activation of the injection device and after return of the needle guard to the protecting position, to prevent re-exposure of the needle.

The activation element can include an inner housing located inside the housing and having trigger projections for maintaining the plunger in an idle position; and a latch located inside the housing and circumferentially surrounding the inner housing, the latch being moveable between a firing position and an armed position. Retraction of the needle guard to the injecting position urges the latch toward the firing position, thereby releasing the trigger projections from the plunger and activating the injection device.

The jet injector can further include an elastomeric element, such as a spring element, that acts upon the needle guard and urges the needle guard toward the protecting position; wherein the elastomeric element returns the needle guard to the protecting position after the medicament has been ejected from the needle, thereby substantially re-enclosing the needle.

The needle is mounted on a needle holder operatively associated with the needle and the distal end of the housing, such that rotation of the needle holder places the needle in fluid communication with the fluid chamber. Preferably, the needle has a tip with a length of approximately 1-5 mm and the medicament is ejected at a pressure between around 100 to 1000 p.s.i. (689 to 6895 kPa) and at a rate of at least 0.40 ml/sec.

The jet injector may also include a removable safety cap operatively associated with the distal end of the injection device such that rotation of the safety cap imparts rotation on the needle. At least a portion of the housing is made of a transparent or translucent material for allowing viewing of the fluid chamber. The medicament is preferably ejected at a pressure between around 100 to 500 p.s.i. (689 to 3448 kPa) and at a rate of about 0.50 ml/sec so that about 1 ml of the medicament is ejected in about 2 seconds.

The fluid chamber may comprise an ampule having a distal end, a proximal end and an opening in each of the distal and proximal ends; a pierceable seal associated with the opening in the distal end; and a stopper located in the proximal end of the ampule for maintaining the medicament inside the ampule. An alternative fluid chamber may be used such that activation of the force generating source moves the pierceable seal towards the injection assisting needle to pierce the seal and moves the stopper to eject medicament from the injection assisting needle.

The present invention also relates to a method of delivering medicament to an injection site of a patient. The method includes the steps of extending a needle from a shield prior to inserting the needle into the needle insertion point, the shield initially concealing the needle; inserting the needle into the needle insertion point to a depth of less than 5 mm, with the needle being in fluid communication with a fluid chamber that contains at least about 0.02 to 2 ml of the medicament; and applying a force sufficient to eject the medicament from the fluid chamber and through the needle to deliver the medicament to the injection site in less than about 2.75 seconds. The needle insertion point is located more superficial than the injection site.

Preferably, the initial pressing of the shield against the injection site causes activation of the energy mechanism and may establish fluid communication between the needle and the fluid chamber. An additional step includes retracting the needle into the shield after the desired amount of medicament has been delivered to the injection site and wherein the applied force for injecting the medicament is sufficient to eject an amount of about 1 to 2 ml of the medicament in less than about 2.5 seconds. The needle has a length of approximately 1-5 mm and the medicament is ejected at a at a pressure between around 100 to 1000 p.s.i. (689 to 6895 kPa) and at a rate of at least 0.40 ml/sec. Preferably, the medicament is ejected at a pressure between around 100 to 500 p.s.i. (689 to 3448 kPa) and at a rate of about 0.50 ml/sec so that about 1 ml of the medicament is ejected in about 2 seconds.

BRIEF DESCRIPTION OF THE DRAWINGS

FIG. 14b is a cross-sectional view of the needle assisted jet injector of FIG. 14a taken along a plane perpendicular to that of FIG. 14a;

FIG. 17 is an elevational view of the ram of the injector of FIGS. 14a and 14b;

FIG. 18a is perspective view of the latch assembly of FIGS. 14a and 14b;

FIG. 18b is a cross-sectional view of the latch assembly of FIGS. 14a and 14b taken along line A-A of FIG. 18a;

FIG. 22b is a cross-sectional view of the needle guard of FIGS. 14a and 14b taken along line A-A of FIG. 22a;

DESCRIPTION OF THE PREFERRED EMBODIMENTS

Figure 1:
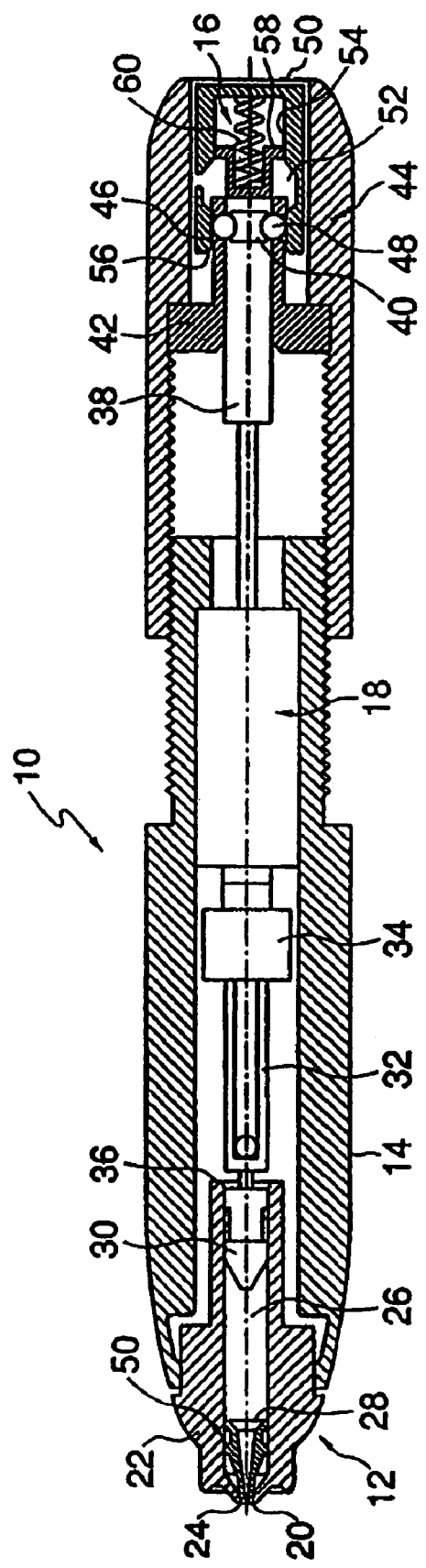
FIG. 1 is a cross-sectional view of a needle assisted jet injector according to the present invention.

For convenience, the same or equivalent elements of the invention of embodiments illustrated in the drawings have been identified with the same reference numerals. Further, in the description that follows, any reference to either orientation or direction is intended primarily for the convenience of description and is not intended in any way to limit the scope of the present invention thereto.

As shown in FIG. 1, a jet injector 10 according to the present invention comprises a nozzle assembly 12 attached to a housing 14. As used in this application, the term jet injection means a particular class of injector that injects medicament by creating a high-speed jet of the medicament that penetrates the tissue of the patient to a distance beyond the exit of the injector. Also, the term distal shall designate the end or direction toward the front of jet injector 10. The term proximal shall designate the end or direction toward the rear of the injector. The term longitudinal designates an axis connecting nozzle assembly 12 to jet injector 10, and the term transverse designates a direction substantially perpendicular to the longitudinal direction including arcs along the surface of jet injector 10, or nozzle assembly 12.

Nozzle assembly 12 can be threadably connected to housing 14 such that it can be readily attached and detached. Alternatively, other known structures for mounting or attaching two components can be utilized as well to detachably mate nozzle assembly 12 to housing 14. In this manner, injector 10 can be reused with various nozzle assemblies that may contain different medications of different doses either together or at different times. For instance, nozzle assembly 12 can be prefilled with medication and disposed of after each use. Further, a medication filling device such as a coupling device can be used to fill the fluid chamber with medication. U.S. Pat. No. 5,769,138 to Sadowski et al., the disclosure of which is herein incorporated by reference, is directed to such a coupling device.

A trigger assembly 16 is located at the proximal end of housing 14. Trigger assembly 16 activates and triggers an energy source or force generating means 18 which forces medicament out of nozzle assembly 12. Energy source 18 can be a coil spring, a gas spring, or a gas propellant.

According to a first embodiment of the present invention, nozzle assembly 12 has an injection assisting needle 20 movable within nozzle assembly 12. Needle 20 will be discussed in detail after first describing the other components of injector 10. The nozzle assembly 12 includes a nozzle member 22 having an opening 24 at the distal end, preferably having a diameter of about 0.04-0.4 inches (1.016 mm to 10.160 mm) or any other suitable diameter that would allow for the introduction of injection assisting needle 20 therein. Nozzle member 22 includes a cylindrical fluid chamber 26 terminating at the distal end in a right circular cone 28. Cone 28 can be a convex cone (as shown), a right circular cone, or any other suitable configuration. A plunger 30 having a pressure wall contoured to cone 28 is positioned to slide within fluid chamber 26. Plunger 30 can include sealing means such as one or more O-rings or the like (not shown) that are formed around its outer periphery to provide a seal, or the plunger itself can be a seal, as described in U.S. Pat. No. 5,062,830, the disclosure of which is incorporated herein by reference. The plunger can also include additional sealing means at spaced intervals to provide a better seal.

Plunger 30 is connected to a ram 32 which in turn is connected to energy source 18. Alternatively, ram 32 can be integrally formed with an energy mechanism if desired. An inertia mass 34 is connected to or integrally formed with ram 32 near the end of ram 32 closest to plunger 30. Inertia mass 34 can be removably connected to ram 32 such that the mass can be adjusted to accommodate different types of injections, taking into consideration, for instance, the viscosity of the medication, the initial pressure build up desired, the strength of energy source 18, and the depth of injection penetration, etc. Inertia mass 34 cooperates with ram retainer 36 to limit the distance that ram 32 can travel toward nozzle assembly 12. One important safety aspect of this feature is that ram 32 cannot become a dangerous projectile if injector 10 is fired when nozzle assembly 12 is not present.

Trigger assembly 16 includes a trigger extension 38 having a trigger engaging notch 40. Trigger extension 38 is attached to the end of ram 32, for example, by a threaded engagement. Trigger assembly 16 also comprises a latch housing sleeve 42 fixedly attached to an actuating mechanism 44. Actuating mechanism 44 is shown as a threaded coupling that operates by rotation movement. Latch housing sleeve 42 has a throughbore dimensioned to allow passage of trigger extension 38. Latch housing sleeve 42 further has a plurality of sidewall openings 46 dimensioned to allow passage of balls or ball bearings 48. A tubular button 50 having one open end and a closed end is telescopingly positioned with latch housing sleeve 42 as shown. Button 50 has a circumferential or annular groove 52 formed on an inner wall 54 thereof to allow portions of the balls 48 to engage groove 52 when trigger assembly 16 is in the fired position, i.e., not engaged with trigger extension 38 (not shown). Balls 48 are positioned so that they are substantially flush with an inner side wall surface 56 of latch housing sleeve 42 to allow trigger extension 38 to pass through latch housing sleeve 42. A latch ball retaining cup 58 is telescopingly positioned within button 50. A compression spring 60 is positioned between the cup 58 and button 50 to bias button 50 and cup 58 away from each other in the axial direction.

Figure 2:
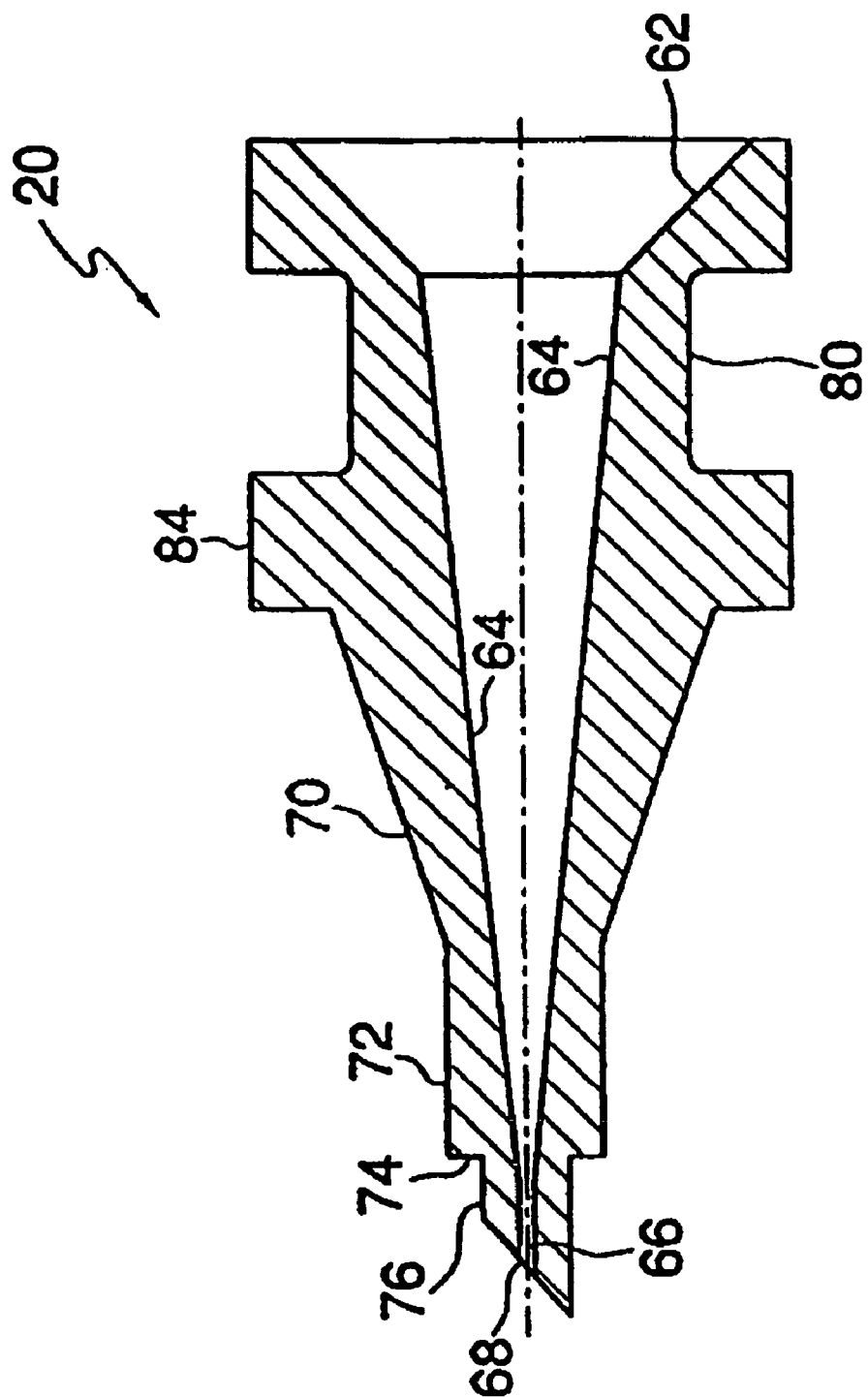
FIG. 2 is a cross-sectional view of the needle on the jet injector of FIG. 1.
Figure 3:
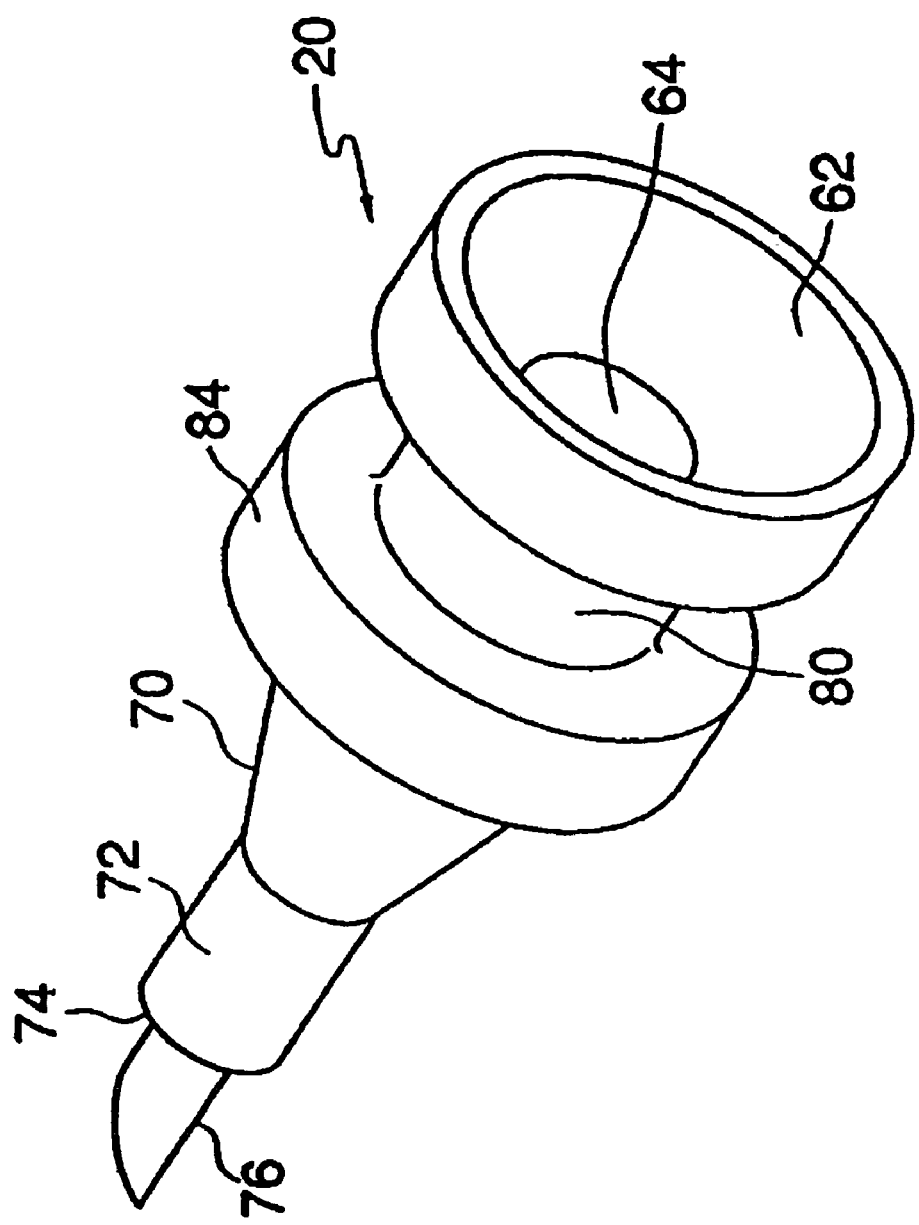
FIG. 3 is a perspective view of the needle of FIG. 2.

The structure of injection assisting needle 20 is best seen in FIGS. 2 and 3. Needle 20 has a plunger receptor 62 at the proximal end which is configured to accommodate plunger 30 as it slides within fluid chamber 26. Although plunger receptor 62 can be of any shape conforming to the exterior profile of plunger 30, it is preferably conical. A needle inner wall 64 is contoured to narrow like a funnel to a needle discharge channel 66 to accelerate the fluid as it is discharged. Needle discharge channel 66 extends to a discharge orifice 68 at the distal end of needle 20. Needle discharge orifice 68 has a diameter of 0.004 to 0.012 inches (0.102 to 0.305 mm). Preferably, the diameter is 0.005 to 0.0075 inches (0.127 to 0.191 mm).

The outer periphery of needle 20 can be of varied geometries such that it fits within fluid chamber 26 of nozzle assembly 12. Advantageously, needle 20 has a conical body section 70 which narrows gradually or tapers towards a cylindrical body section 72 of smaller circumference. Preferably, a shoulder 74 is positioned to separate a needle tip 76 from cylindrical body section 72. Needle tip 76 is also cylindrical, but has a smaller circumference than cylindrical body section 72 such that needle tip 76 can fit within and extend through opening 24 of nozzle assembly 12. However, cylindrical body section 72 of needle 20 has a circumference such that shoulder section 74, existing at the transition between cylindrical body section 72 and needle tip 76, prevents cylindrical body section 72 from existing within opening 24. The length of needle tip 76 from its end to shoulder 74 is approximately 1 to 5 mm. Thus, needle tip 76 will penetrate the skin to a depth less than 5 mm. It should also be noted that although needle tip 76 is shown having a single beveled end at a 45° angle, needle tip 76 can have any shape that penetrates the skin.

Figure 4:
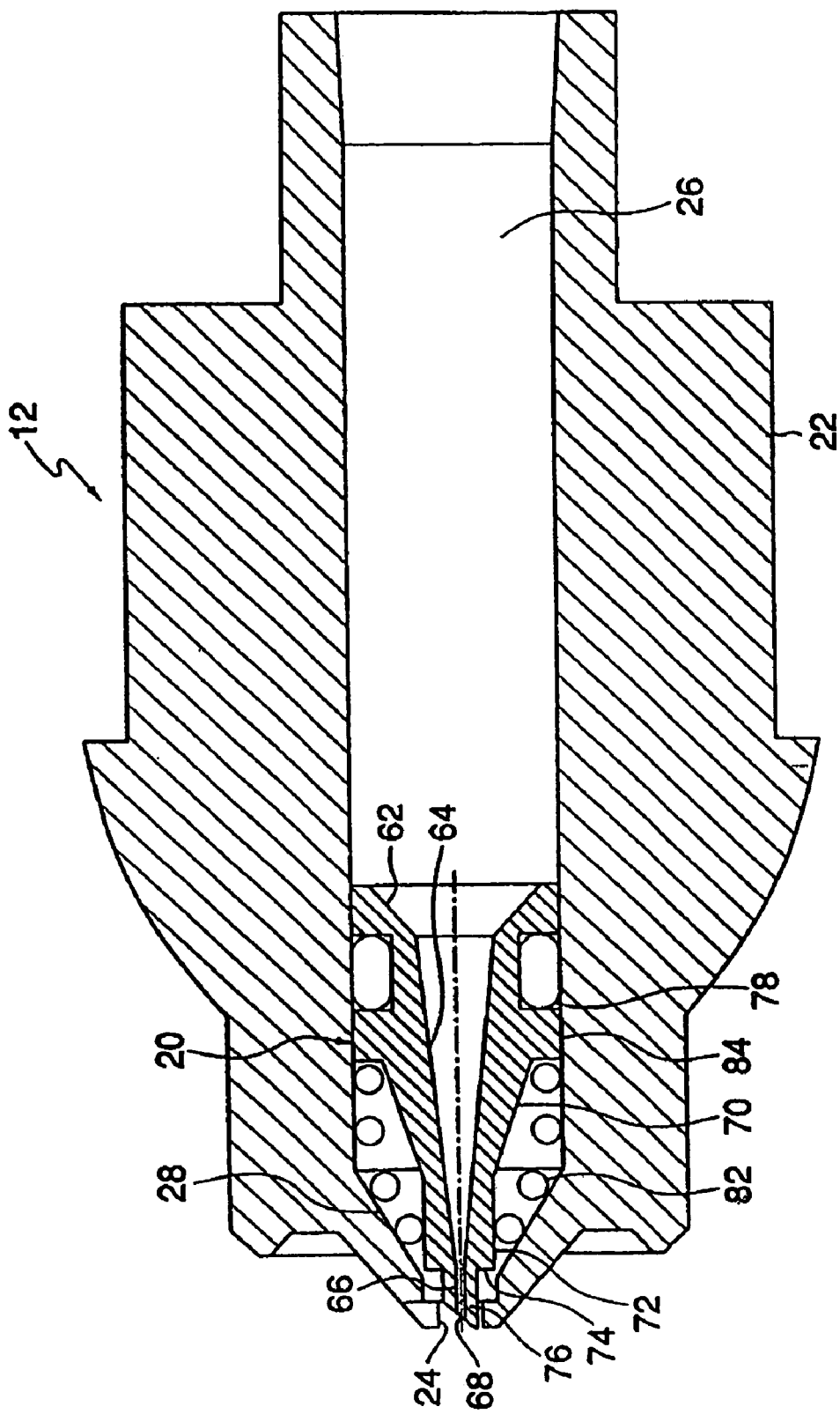
FIG. 4 is an enlarged cross-sectional view of the jet injector of FIG. 1 with the needle in the retracted position.
Figure 5:
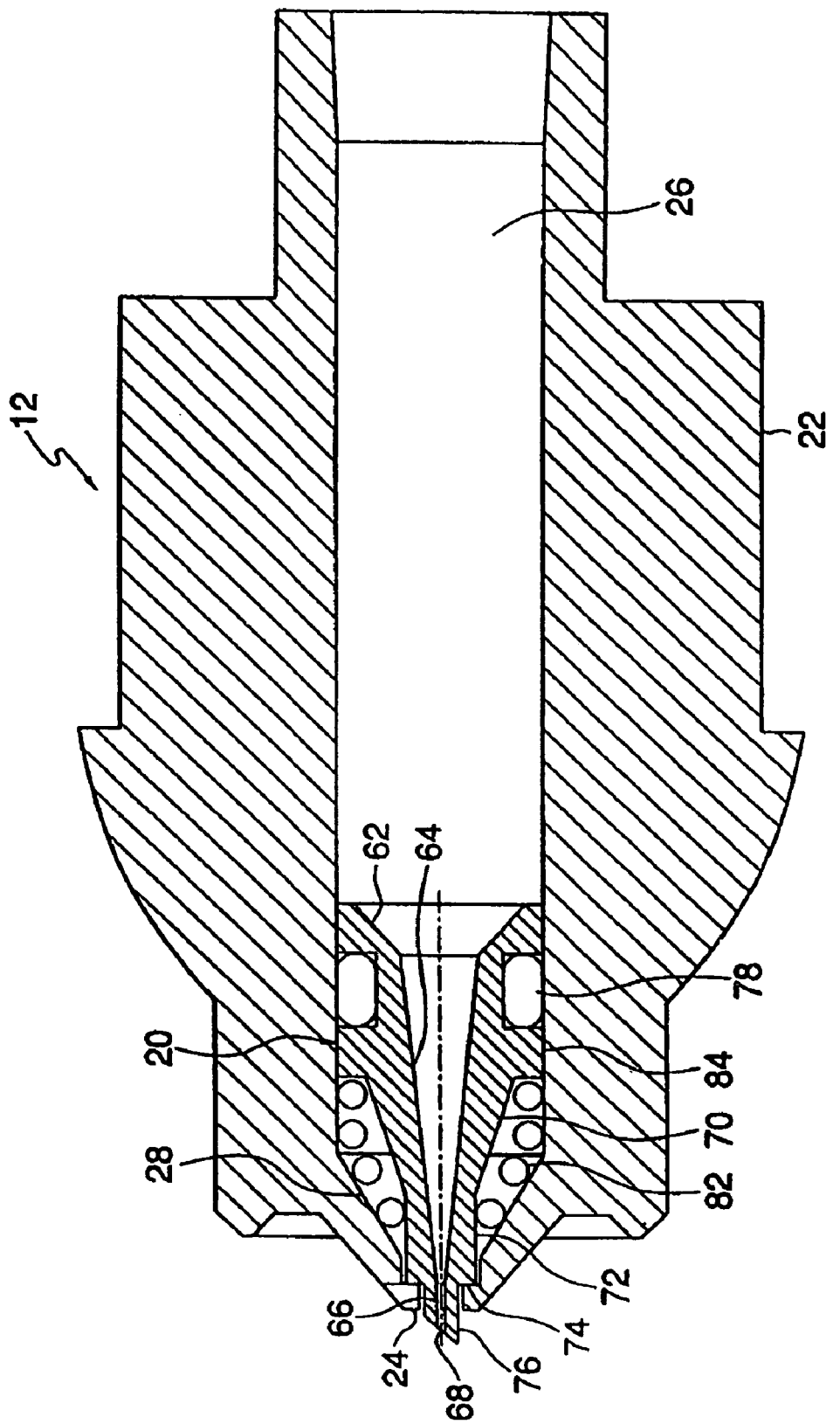
FIG. 5 is an enlarged cross-sectional view of the jet injector of FIG. 1 with the needle in the extended position.

As shown in FIGS. 4 and 5, needle 20 is positioned coaxially and retractably within the distal end of fluid chamber 26 such that when injector 10 is fired, needle tip 76 extends out opening 24 of nozzle assembly 12 at a speed sufficient to penetrate the outer layer of skin. By inserting needle tip 76 to a depth less than 5 mm, typically only the epidermis of the skin is penetrated and the pressure needed to deliver the medicament to the desired region by jet injection is lower than that would otherwise be needed with needleless jet injection. While delivery of medicament by syringes and auto-injectors is limited by the length of the needle, the needle assisted jet injector according to the present invention delivers the medicament to a depth deeper than the length of the needle. This depth can include any region of the skin and beyond including intradermal, subcutaneous, and intramuscular.

To provide a seal between needle 20 and fluid chamber 26, needle 20 includes a sealing means such as an O-ring 78 or the like formed around the outer periphery of needle 20 and accommodated by slot 80. In an alternative embodiment shown in FIG. 6, needle 120 itself is the seal. Thus, slot 80 is not needed. Needle 120 also differs from needle 20 in that cylindrical body section 72 is absent so that conical body section 70 terminates at shoulder 74.

FIG. 5 illustrates injection assisting needle 20 in its extended position. Needle tip 76 extends beyond the distal end of nozzle assembly 12. Shoulder 74 abuts the bored out inner section of nozzle opening 24 to prevent needle 20 from extending beyond needle tip 76. A retraction element 82, in this embodiment a spring, is compressed to provide a recoil force once the medicament is expelled so that needle tip 76 will retract back into nozzle opening 24. Needle 20 preferably has a ridge 84, the distal surface of which provides an annular area for the compression of retraction element 82. Alternatively, a washer can be used instead of the ridge 84 to contain O-ring 78 and compress the retracting mechanism during operation.

Figure 6:
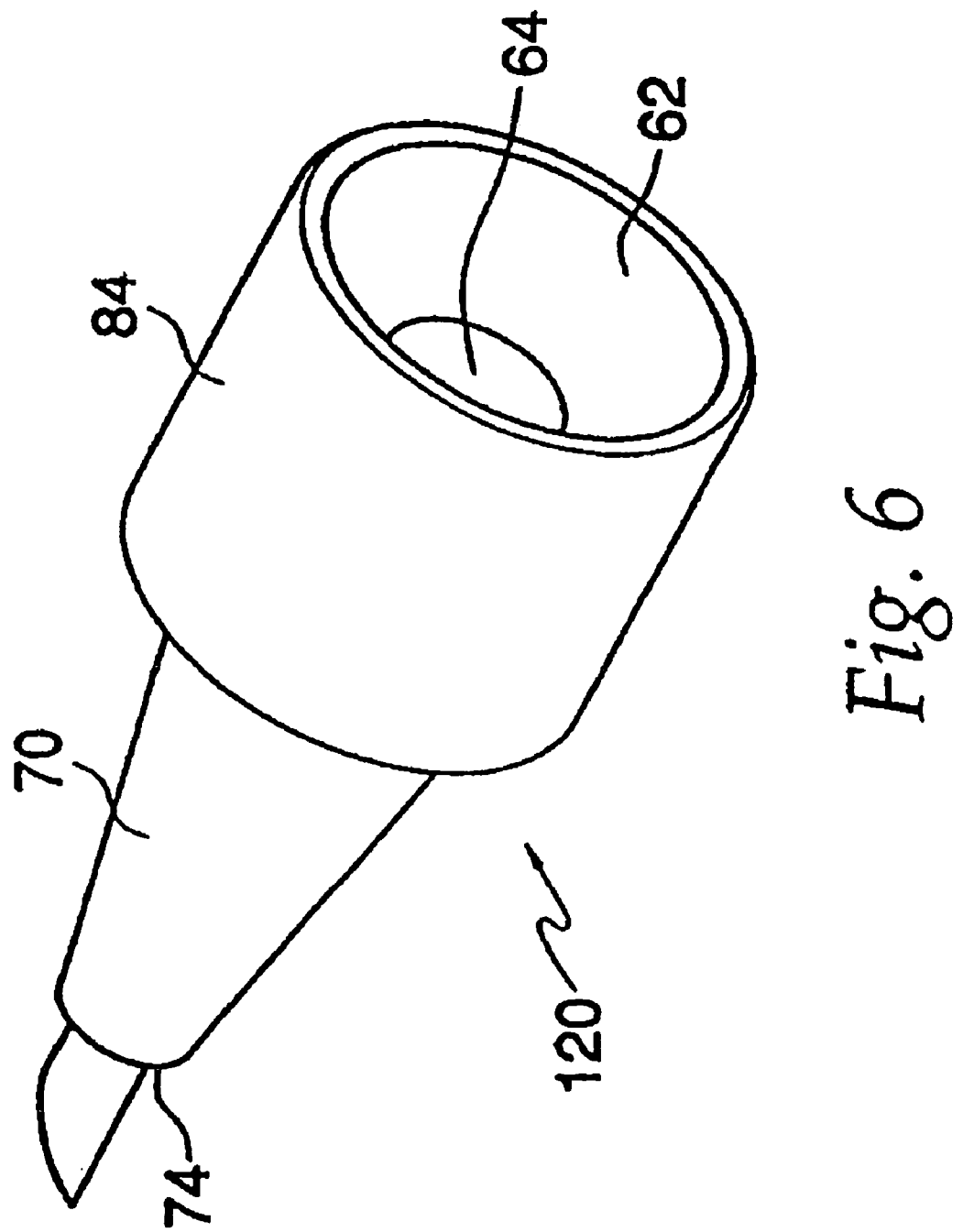
FIG. 6 is a perspective view of a second embodiment of the needle according to the present invention.
Figure 7:
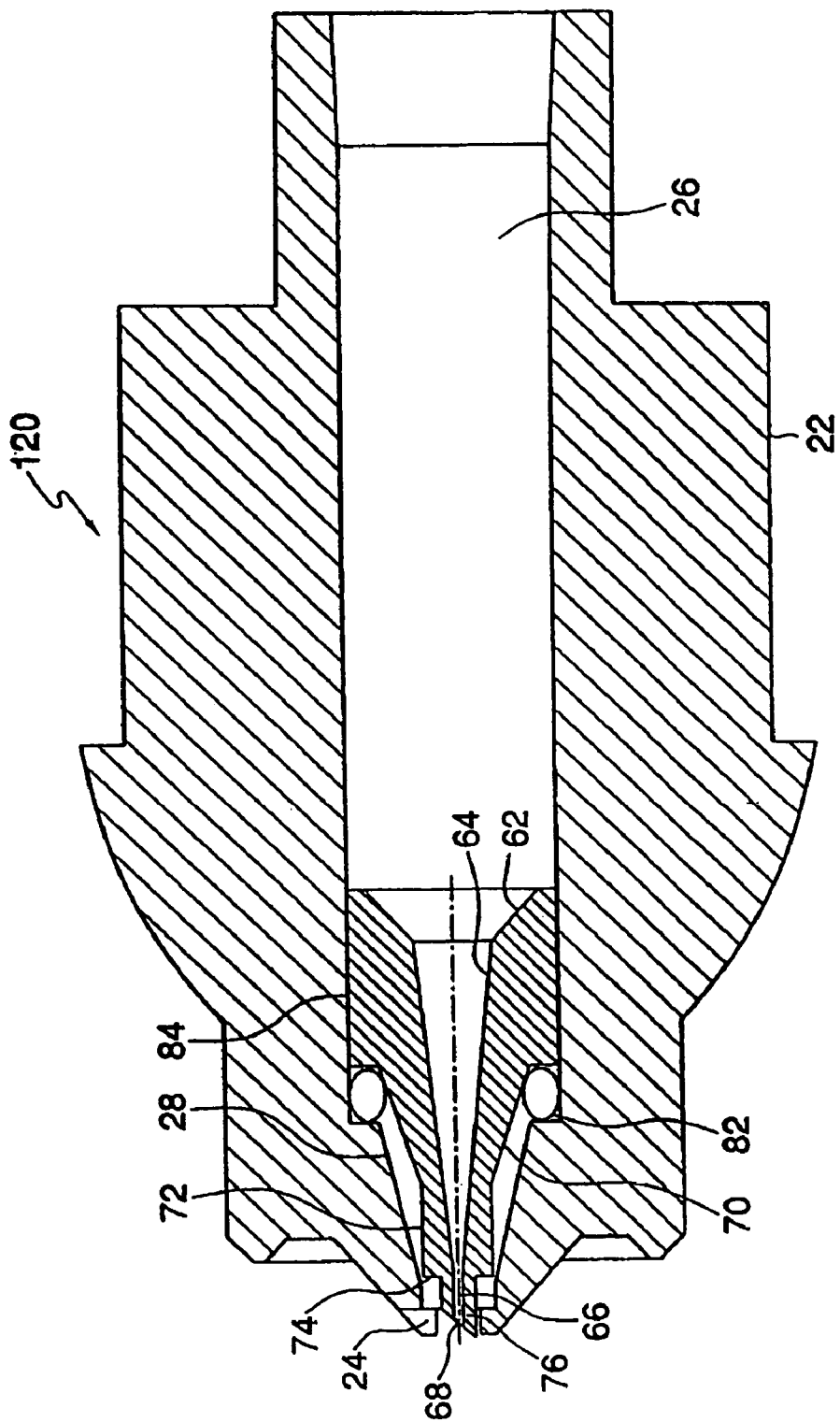
FIG. 7 is a partial cross-sectional view of a jet injector according to the present invention with the needle of FIG. 6 in the retracted position.
Figure 8:
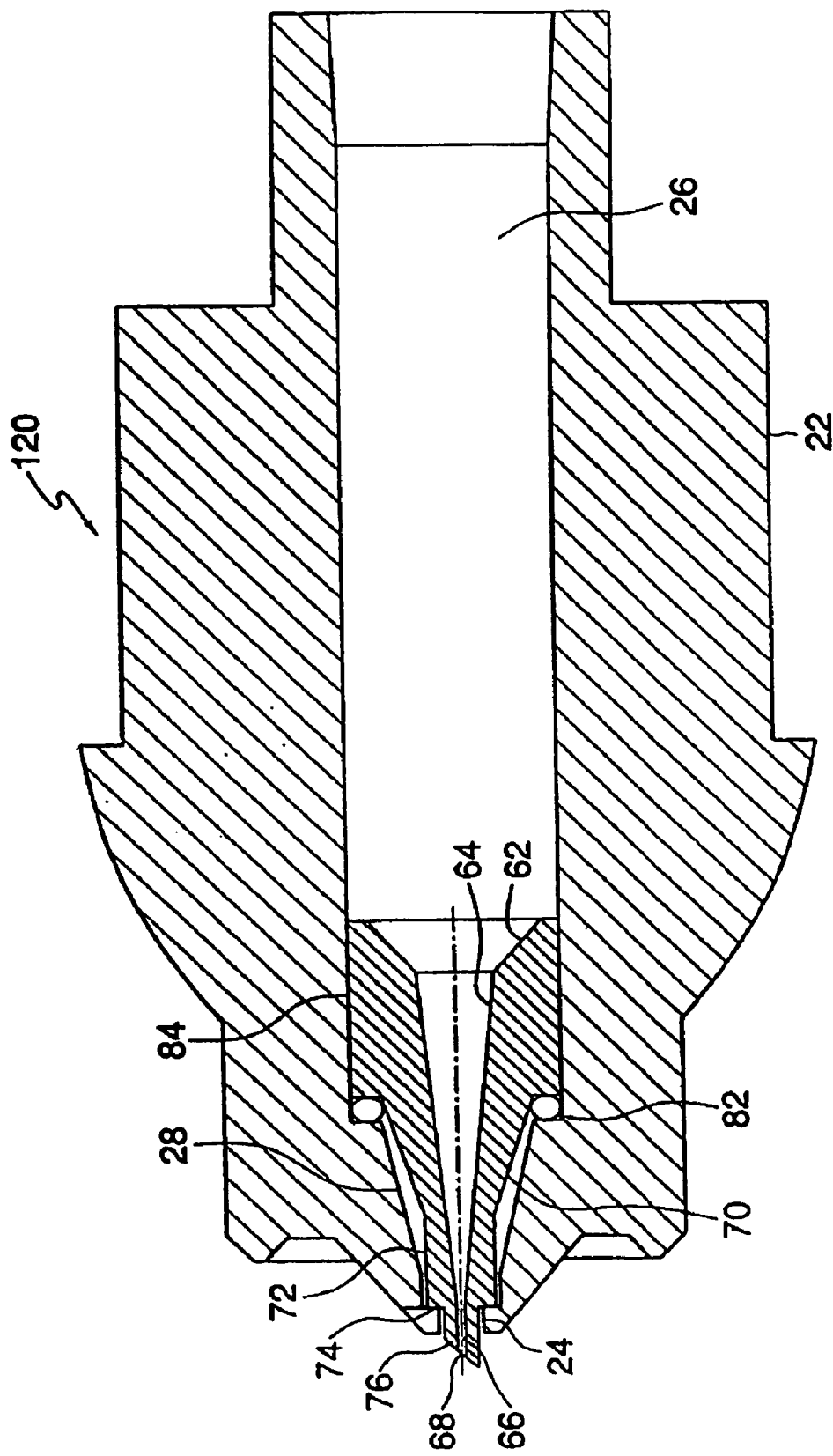
FIG. 8 is a partial cross-sectional view of a jet injector according to the present invention with the needle of FIG. 6 in the extended position.

FIGS. 7 and 8 show needle 120 of FIG. 6 with nozzle assembly 12 in which retraction element 82 is a resilient O-ring or other like material known to those skilled in the art. When an O-ring is used as retraction element 82, it can also act as a sealing mechanism, and for this reason the O-ring is preferred. The interior of needle 120 is similar to that of needle 20. FIG. 7 illustrates needle 120 in the retracted condition, before expelling medicament, and FIG. 8 shows the extended condition during which medicament is expelled. Similar to embodiments previously described, this embodiment functions to extend the needle tip 76 beyond nozzle opening 24 and penetrate the outer layer of the patient's skin during operation. Also, similar to embodiments previously described, needle 120 also preferably has ridge 84 around the proximal end to provide a surface which compresses the resilient material when the injector is triggered.

Figure 9:
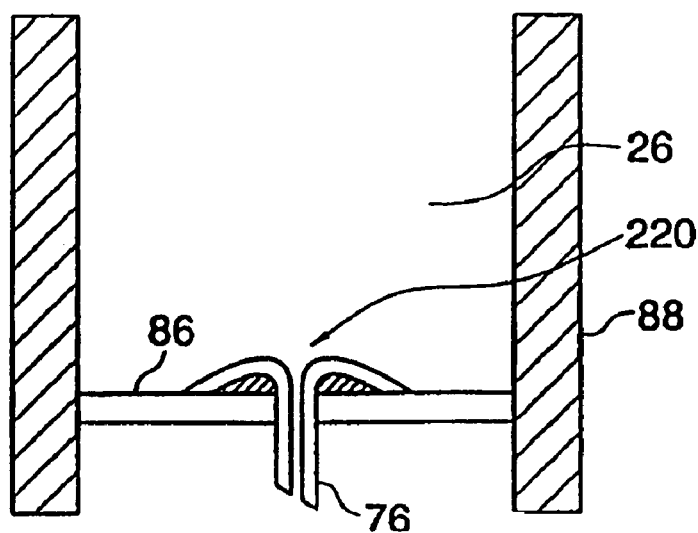
FIG. 9 is a cross-sectional view of another embodiment of the present invention with a flexible member as the retraction element and the needle in the retracted position.
Figure 10:
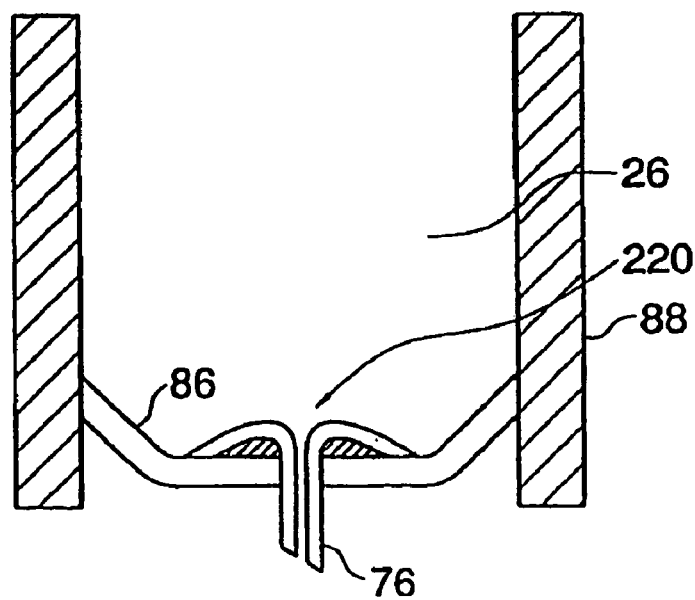
FIG. 10 is a cross-sectional view of the embodiment of FIG. 9 with the needle in the extended position.

Another embodiment of the present invention, shown in FIGS. 9 and 10, uses a flexible member 86 as the retraction element. FIG. 9 illustrates the neutral condition before expelling the medicament. Flexible membrane 86 spans between walls 88 of nozzle assembly 12 which define fluid chamber 26 for holding medicament. Similar to embodiments previously described, the distal end of nozzle walls 88 act to conceal needle tip 76 until the injector is fired. Needle 220 is attached to flexible membrane 86 by any conventional means known to those skilled in the art. Preferably, needle 220 is integrally attached to flexible membrane 86 with an adhesive. FIG. 10 shows needle 220 in its extended position where the needle tip 76 extends beyond the end of walls 88 such that needle tip 76 penetrates the outer layer of skin to allow injection and deliver of the medicine at reduced pressure.

Other embodiments of the present invention relate to injectors with a fixed needle, i.e. a non-retracting needle that permanently extends beyond the nozzle assembly. Both a one-piece and a two-piece nozzle assembly with a fixed needle can be used and are contemplated by this invention.

Figure 11:
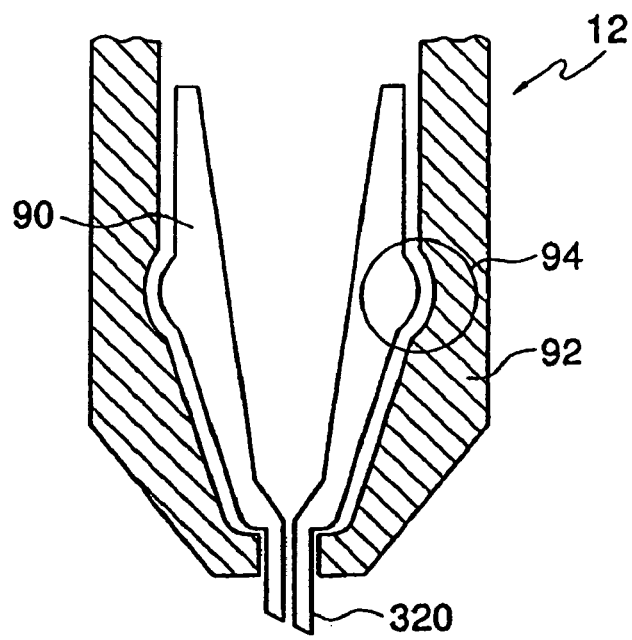
FIG. 11 is a cross-sectional view of a two piece nozzle assembly having a fixed needle.
Figure 12:
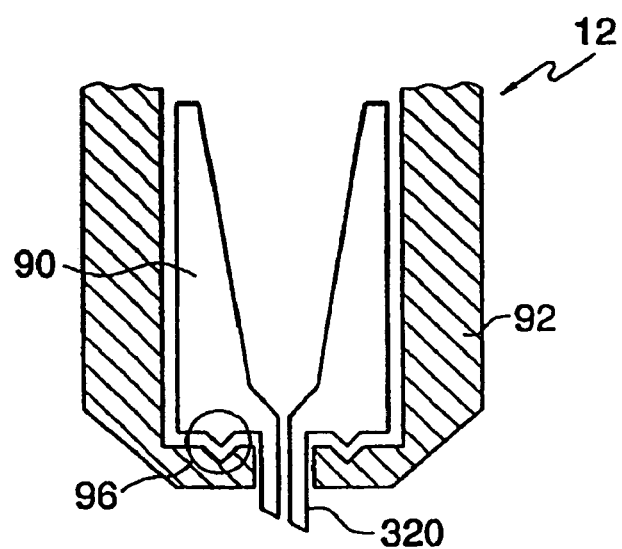
FIG. 12 is a cross-sectional view of another embodiment of a two piece nozzle assembly having a fixed needle.

FIGS. 11 and 12 show embodiments of the present invention with a two piece nozzle assembly with a fixed needle 320. A first section 90 of nozzle assembly 12 has needle 320 at the distal end and can either be attached internally or externally to a second section 92 to form nozzle assembly member 12. Although any conventional attaching means can be used, such as solvent or adhesive bonding, FIG. 11 shows a preferable friction-fitting or snapping attaching means 94 for both internal and external attachment of first section 90 and second section 92. FIG. 12 shows a preferable ultrasonic bonding means 96 of attachment. Although ultrasonic bonding features 96 can be placed at any location to attach the two pieces, preferably, the ultrasonic bonding features 96 are along the distal end at the interface between first and second sections 90, 92 to facilitate ease of manufacturing.

Figure 13:
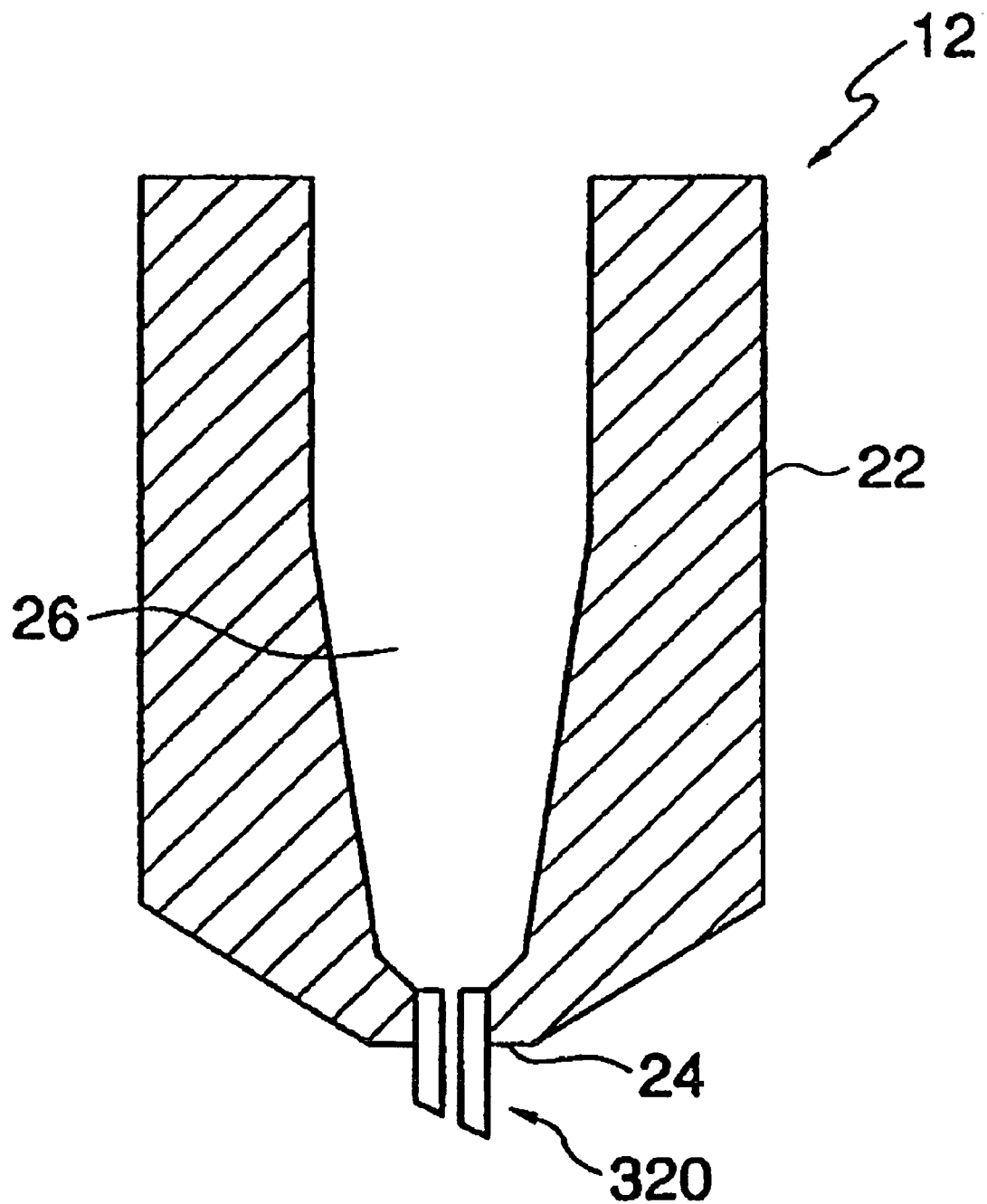
FIG. 13 is a cross-sectional view of another embodiment of a two piece nozzle assembly having a fixed needle.

Another embodiment of a multi-piece nozzle assembly with fixed needle 320 is shown in FIG. 13. The nozzle assembly consists of nozzle member 22 having an opening 24 designed to receive a tubular insert to create fixed needle 320. Although FIG. 13 shows a multi-piece nozzle assembly, fixed needle 320 can be made to be integral with nozzle assembly 12.

Figure 14A:
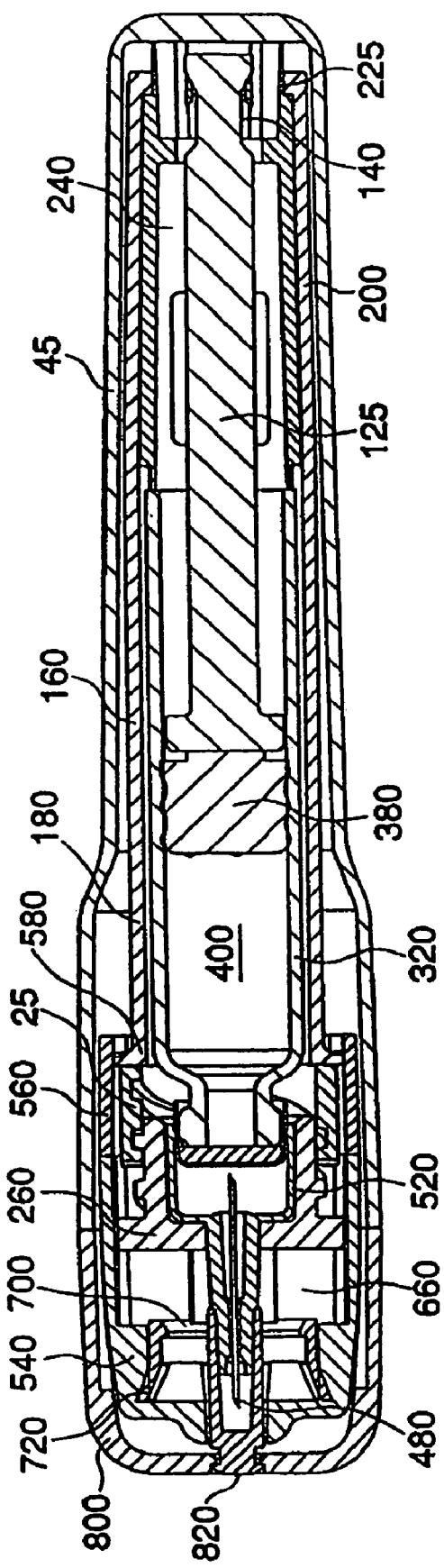
FIG. 14a is a cross-sectional view of a needle assisted jet injector according to a preferred embodiment of the present invention.
Figure 14B:
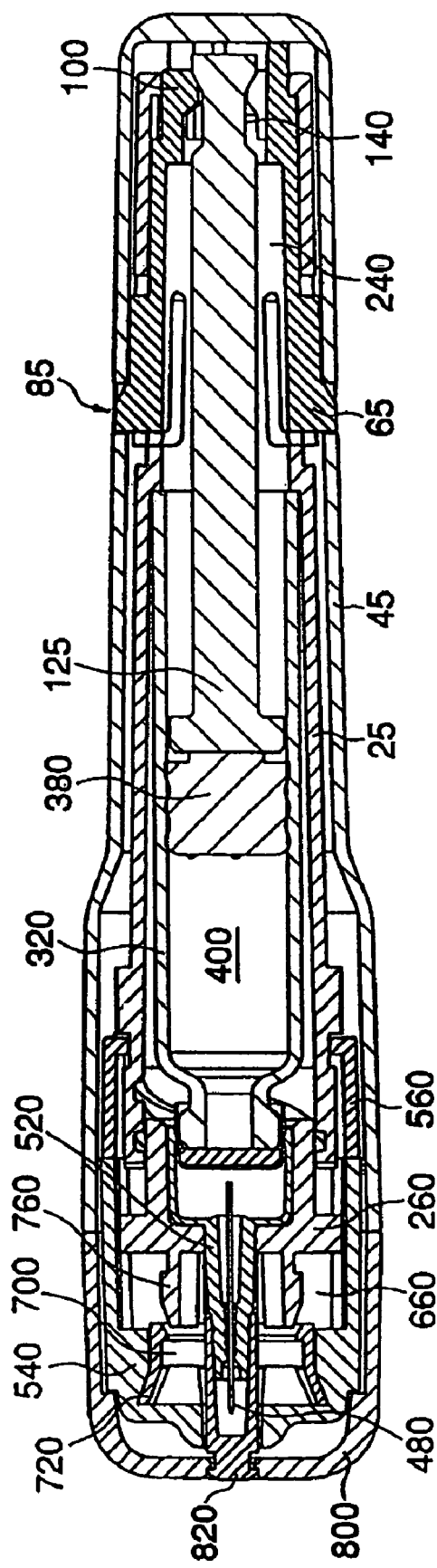
Figure 15:
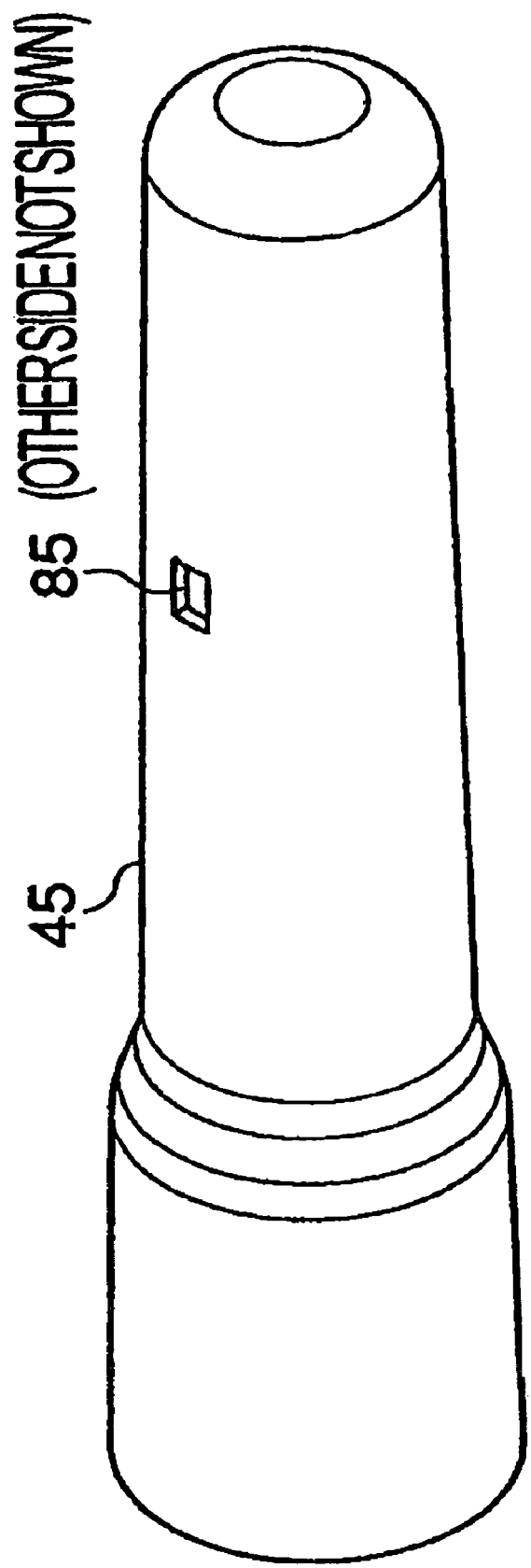
FIG. 15 is a perspective view of the outer housing of the needle assisted jet injector of FIGS. 14a and 14b.
Figure 16:
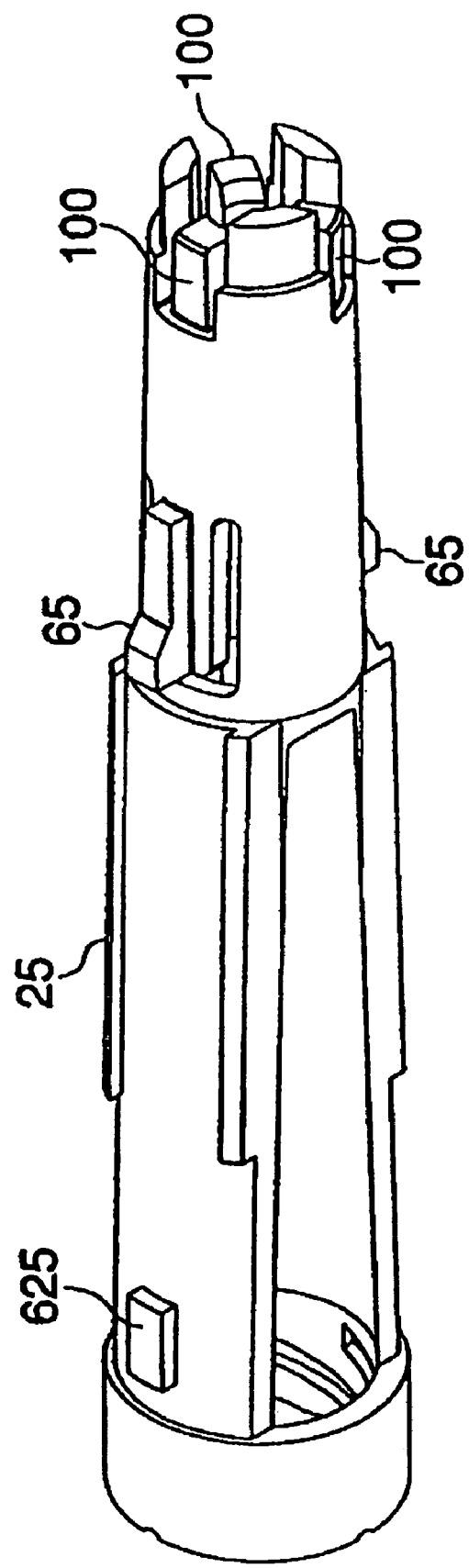
FIG. 16 is a perspective view of the inner housing of the injector of FIGS. 14a and 14b.

FIG. 14a and FIG. 14b depict a preferred embodiment of the present invention having a retractable shield around the needle. An inner housing 25, shown in FIG. 16, snaps inside an outer housing 45, using a pair of snaps 65 located on the inner housing 25. The snaps 65 protrude through openings 85 in the outer housing 45, shown in FIG. 15, and maintain the inner housing 25 and the outer housing 45 in a fixed relationship with one another. Other techniques known in the art, such as gluing and welding, could be used to hold the inner housing 25 and outer housing 45 together.

Figure 18B:
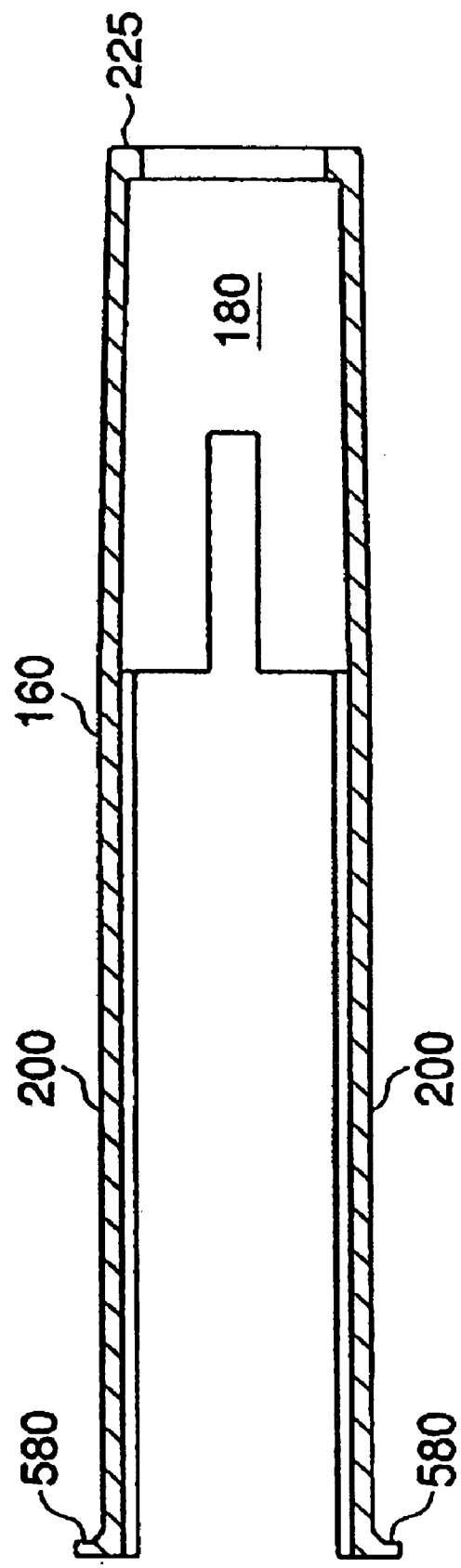

The inner housing 25 has three trigger protrusions 100 extending from its distal end. These trigger protrusions 100 are shaped to mate with an annular recess 140 in ram 125 (FIG. 17). Ram 125 is urged toward the distal end of the injector with a compression spring 240, however other energizing devices capable of producing an injection of up to 2 ml in about 2.5 seconds or less could be used. These energizing sources typically include rubber elastomers and compressed gas cartridges. A latch 160, shown in FIG. 18a, is slidable inside the outer housing 45 and surrounds the inner housing 25. The latch 160 has a barrel portion 180 at its distal end and a pair of extensions 200 at its proximal end. When the jet injector is ready to be fired, ridge 225 on the barrel portion 180, shown in FIG. 18b, contacts the trigger protrusions 100 and maintains them in the annular recess 140 in ram 125, preventing the ram 125 from firing under the force of compression spring 240.

Figure 19:
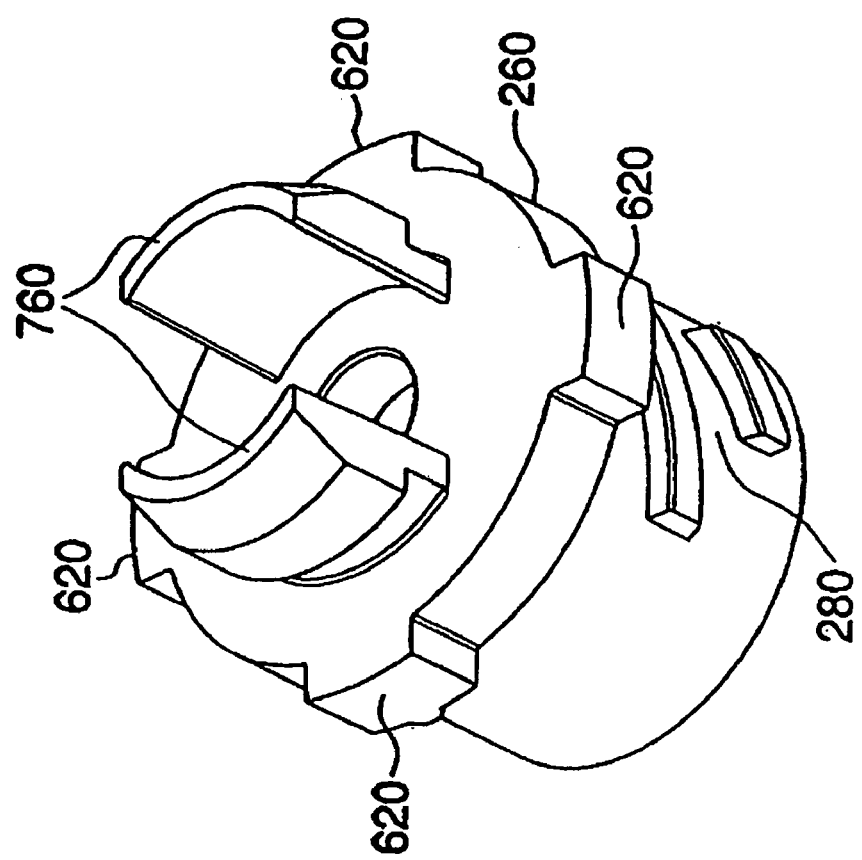
FIG. 19 is a perspective view of the needle holder of FIGS. 14a and 14b.
Figure 20A:
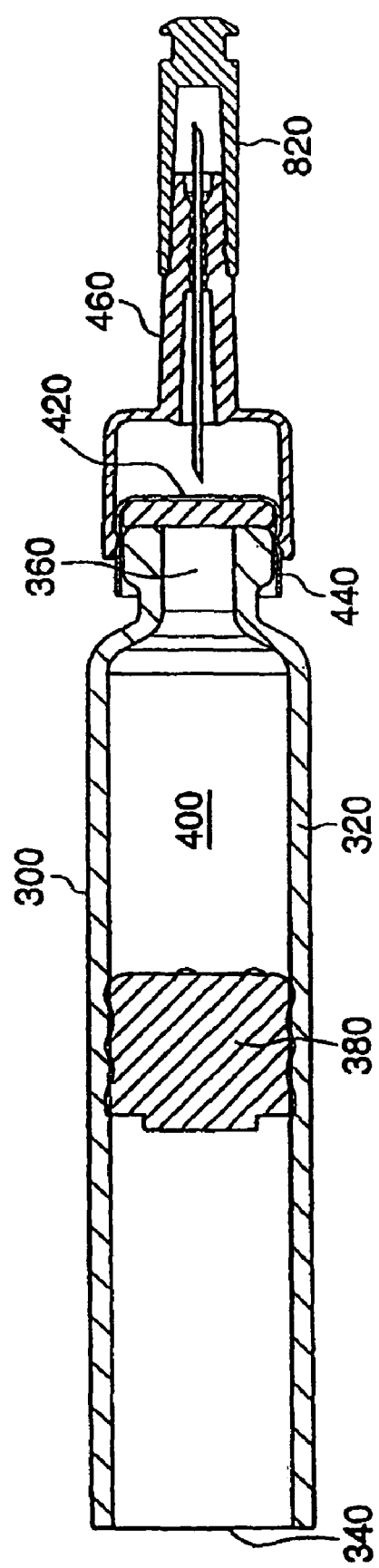
FIG. 20a is a cross-sectional view of the cartridge assembly of FIGS. 14a and 14b.

A needle holder 260, shown in FIG. 19, mounts onto the inner housing 25 with right hand threads 280 and holds a cartridge assembly 300 inside the inner housing 25. As best shown in FIG. 20a, the cartridge assembly 300 consists of a glass ampule 320 having an opening 340 in its proximal end and a seal 360 on its distal end. The glass ampule 320 typically holds between 0.02 and 2 mL of a medicament 400. Instead of glass, the ampule 320 can also be constructed of metal or other suitable materials known in the art. A rubber stopper 380 is slideable within the glass ampule 320 and seals the opening 340 in its proximal end of the glass ampule 320 so the medicament 400 stays inside the glass ampule 320. The seal 360 on the distal end comprises a rubber seal 420 formed on the end of the ampule 320 by conventional techniques, such as an aluminum cap 440 having a hole in its end. The ram 125 extends into the opening 340 in the proximal end of the glass ampule 320 and abuts the rubber stopper 380. To provide a visual indication of the device's status, at least a portion of the outer housing 45 is constructed of transparent or translucent material, so that the cartridge assembly 300 can be viewed by the user.

Figure 21A:
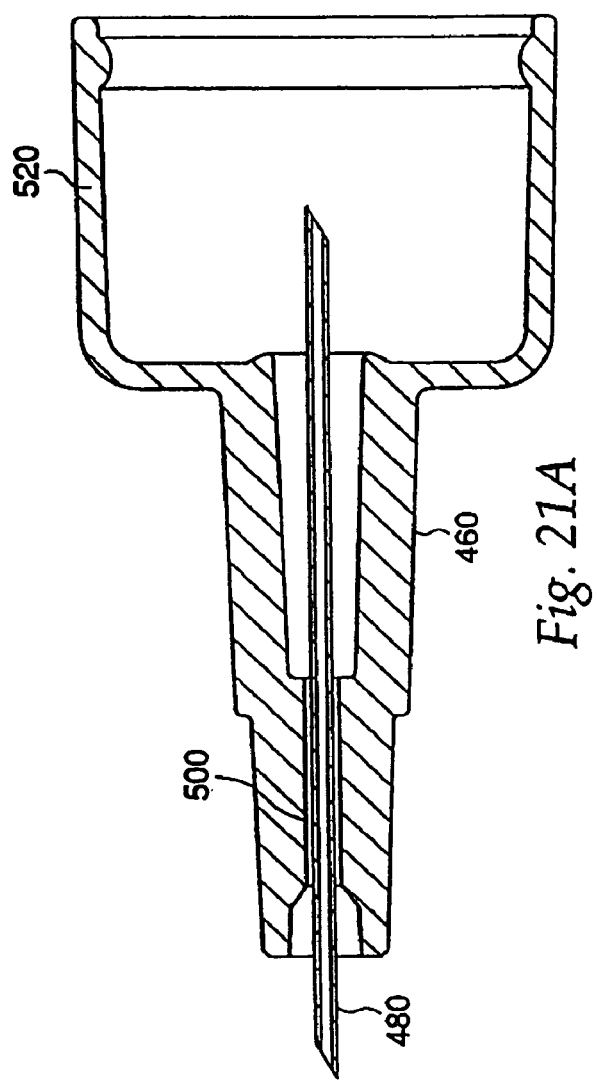
FIG. 21a is a cross-sectional view of the needle assembly of FIGS. 14a and 14b.

A needle assembly 460, shown in FIG. 21, consists of an injecting needle 480 glued inside a longitudinal pocket 500 in the needle hub 520. Grooves or other surface treatment on the longitudinal pocket 500 and on the injecting needle 480 enhance bonding between the injecting needle 480 and the needle hub 520. Alternatively, other known methods of fixing, such as molding, may be used to secure the injecting needle 480 to the needle hub 520.

Figure 21B:
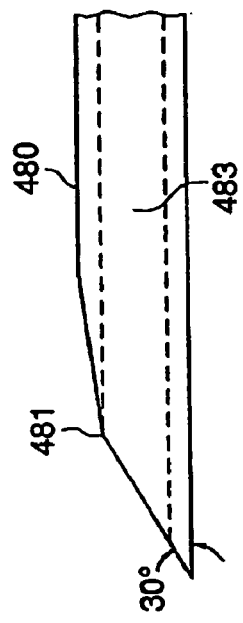
FIG. 21b is a cross-sectional view of the injecting needle of FIGS. 14a and 14b.

To allow for an appropriate injection time, the injecting needle 480 is of 27 gauge, however other gauges may be suitable for different applications. The length of the needle 480 that extends beyond the distal end of the needle hub 520, and is used for injection, is preferably between 1 and 5 mm. As shown in FIG. 21b, the injecting needle 480 preferably has a 30 point. This angle decreases the length of the bevel 481 and thereby increases the effective length of the lumen 483. The increase in the effective length of the lumen 483 reduces the percentage of incomplete injections.

Needle assembly 460 is mounted to the needle holder 260, and clockwise rotation of the needle holder 260 approximately one quarter of a turn threads it further into the inner housing 25 and forces the proximal end of the injecting needle 480 through rubber seal 420, thereby creating the drug path.

Figure 22A:
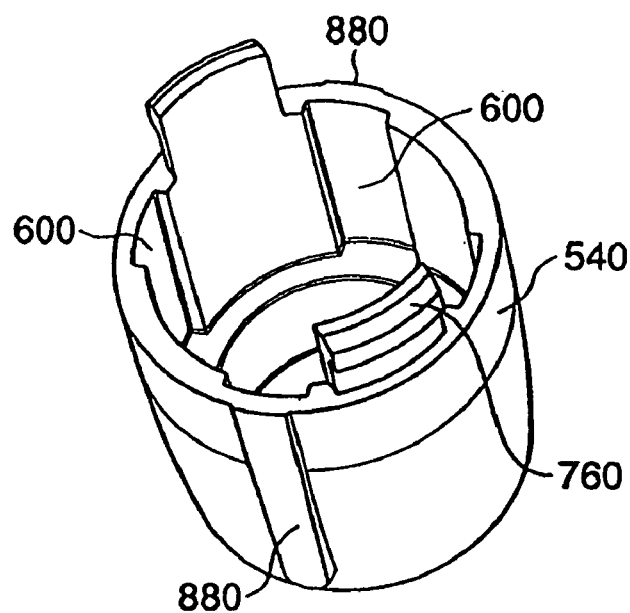
FIG. 22a is a perspective view of the needle guard of FIGS. 14a and 14b.
Figure 23A:
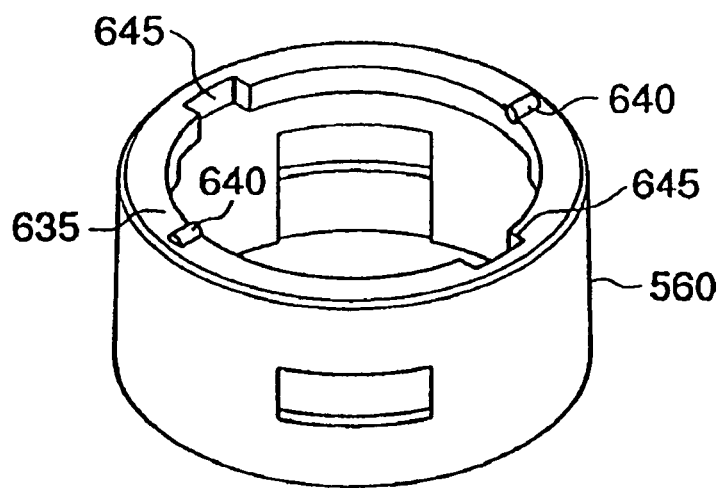
FIG. 23a is a perspective view of the needle guard cap of FIGS. 14a and 14b.
Figure 23B:
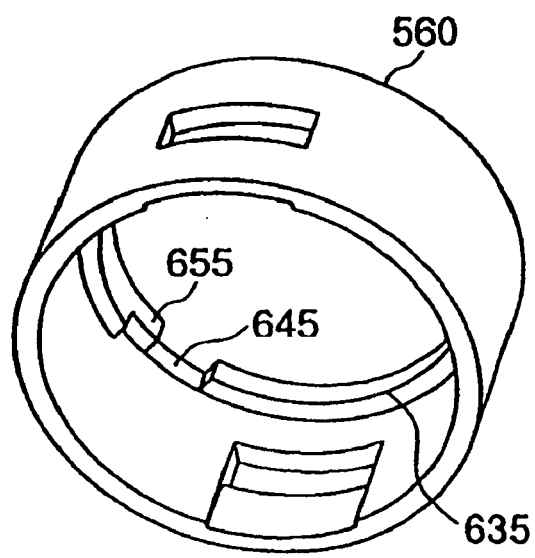
FIG. 23b is a perspective view of the needle guard cap of FIGS. 14a and 14b.

A needle guard 540, depicted in FIG. 22a, is located at the distal end of the injecting device and conceals the injecting needle 480. The needle guard 540 snaps together with the needle guard cap 560, which is shown in FIGS. 23a and 23b. The needle guard cap 560 slides on extensions 200 of the latch 160, thereby allowing the needle guard 540 to slide longitudinally on the distal end of the injector to expose the injecting needle 480. Feet 580 at the end of extensions 200 prevent the needle guard cap 560 and consequently the needle guard 540 from sliding completely off the end of the device.

Recesses 600 in the needle guard 540 and corresponding bosses 620 on the needle holder 260 translate any rotation of the needle guard 540 into rotation of the needle holder 260. Abutments 655 on the inner surface of the needle guard cap 560, shown in FIG. 23b, are positioned relative to the feet 580 of the latch 160 to inhibit counter-clockwise rotation of the needle holder 260. This prevents the user from unscrewing the device and removing the cartridge assembly 300 from it.

The needle guard cap has a inner flange 635 with a pair of cutouts 645 therein. The cutouts 645 correspond to the pair of bosses 625 on the inner housing 25. The flange 635 acts to prevent motion of the needle guard cap 560 and the needle guard 540 toward the proximal end of the device unless the cutouts 645 are rotated into alignment with the pair of bosses 625. This acts as a safety feature to prevent accidental firing of the injector. Alternatively, other known mechanisms, such as a removable safety strip can be used to prevent accidental firing of the injector.

A return spring 660 rests on the needle holder 260 and urges the needle guard 540 toward the distal end of the injector, thereby keeping the injecting needle 480 concealed. A pair of stops 640, shown in FIG. 23, extend from the needle guard cap 560 and are positioned relative to bosses 625 on the inner housing 25 such that the needle guard 540 and needle holder 260 cannot rotate clockwise under the force of return spring 660.

Pressing the needle guard 540 toward the proximal end of the device causes the needle guard cap 560 to push the latch 160 longitudinally toward the proximal end of the device, thereby moving the ridge 225 on the barrel portion 180 of the latch 160 off the trigger protrusions 100 on the inner housing 25. This allows the trigger protrusions 100 to flex out of the annular recess 140 in the ram 125, thereby causing the ram 125 to fire under the force of compression spring 240. When the ram 125 fires, it slides rubber stopper 380 in the glass ampule 320 toward the distal end of the device, causing the medicament 400 to flow through the drug path (created by turning the needle holder 260 clockwise one quarter turn prior to firing, as discussed above) and eject from the injecting needle 480.

Figure 22B:
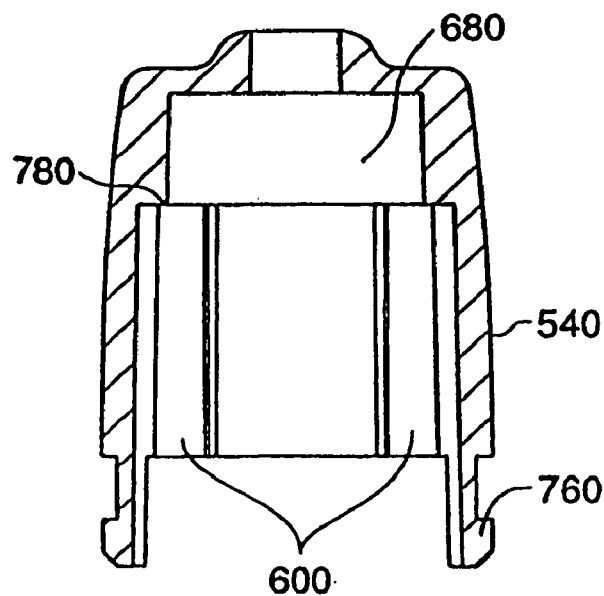
Figure 24:
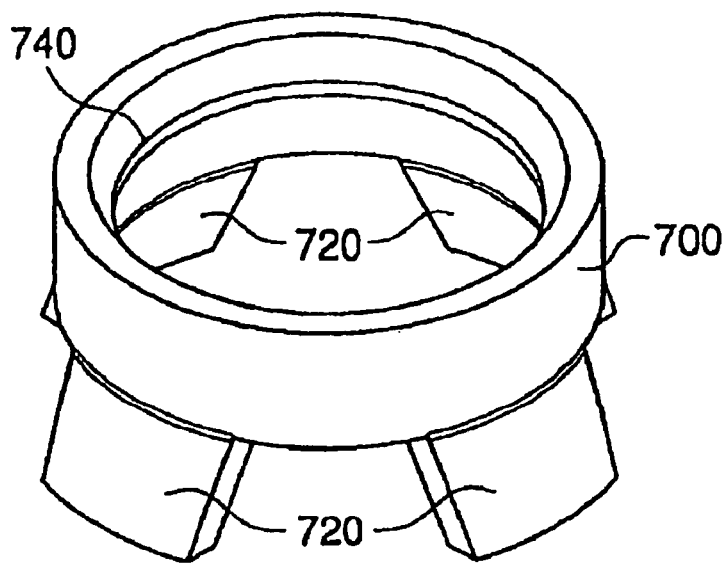
FIG. 24 is a perspective view of the locking ring of FIGS. 14a and 14b.

As depicted in FIG. 22b, needle guard 540 has a pocket 680 located therein. A locking ring 700, shown in FIG. 24, sits in pocket 680 and prevents re-exposure of the injecting needle 480 after the device has been fired. Locking ring 700 has multiple splayed legs 720 and an undercut 740 that mates with extensions 760, which protrude from the needle holder 260. Upon depression of the needle guard 540 toward the proximal end of the device, extensions 760 engage the undercut 740 and become locked thereon. When the needle guard 540 returns to its original position, the locking ring 700 is pulled from pocket 680 in the needle guard 540 and splayed legs 720 expand radially outward. Upon an attempt to re-depress the needle guard 540, splayed legs 720 catch shoulder 780 on the needle guard 540 and restrict further movement of the needle guard 540, thereby preventing re-exposure of the injecting needle 480.

Figure 25:
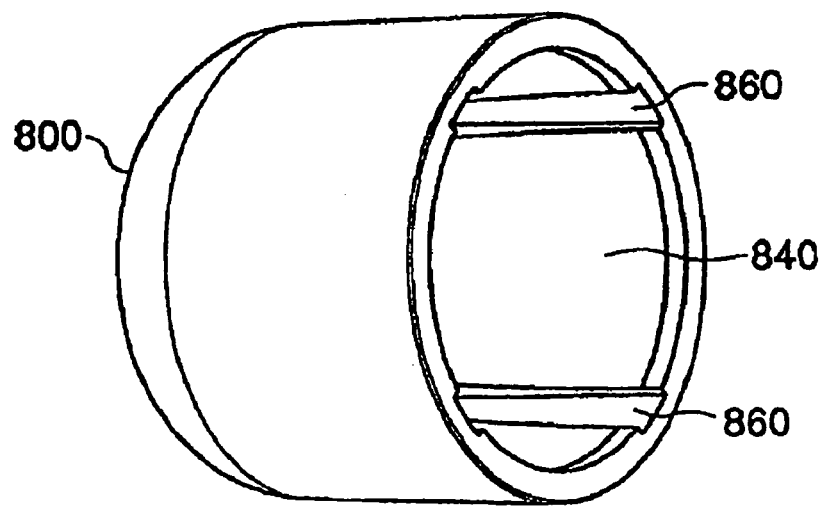
FIG. 25 is a perspective view of the safety cap of FIGS. 14a and 14b.
Figure 26:
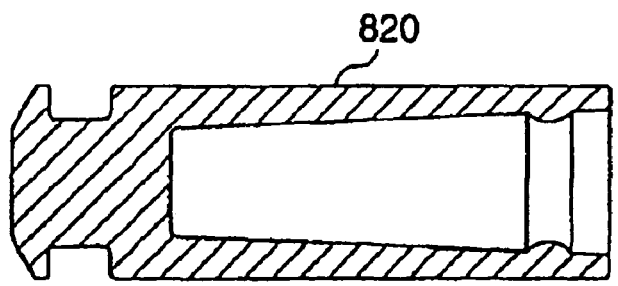
FIG. 26 is a cross-sectional view of the needle cap of FIGS. 14a and 14b.

The device also features a removable safety cap 800 that slides over the needle guard 540 and covers the device prior to its use. The safety cap 800 includes a needle cap 820 (FIG. 26) connected thereto, the needle cap 820 forming a sterile barrier around the needle assembly 460. As shown in FIG. 25, the safety cap 800 has four longitudinal recesses 860 equally displaced about its inner surface 840. These longitudinal recesses 860 are dimensioned to accept two or more bosses 880 located at corresponding locations on the needle guard 540. Because of these two features, clockwise rotation of the safety cap 800 causes corresponding rotation of the needle guard 540 and the needle holder 260. Thus, the user may turn the safety cap 800 clockwise one quarter turn, prior to removing it from the device, to create the drug path and prepare the device for injection.

The device of the preferred embodiment is operated by first turning the safety cap 800 clockwise one quarter of a turn, to create the drug path by inserting the proximal end of injecting needle 480 into the ampule 320. Rotating the safety cap 800 also aligns the cutaways 645 in the safety cap 560 with the bosses 625 on the inner housing 25, allowing the needle guard 540 to be depressed. Next the safety cap 800 and consequently the needle cap 820 are removed from the device. As the distal end of the device is pressed against the injection site, the needle guard 540 moves longitudinally toward the proximal end of the device and the injecting needle 480 enters the skin to a depth of between 1 and 5 mm. The movement of the needle guard 540 causes the ram 125 to fire and consequently between 0.02 and 2.0 ml of medicament 400 is forced out of the ampule 320 and through the drug path in under about 2.75 seconds. Once the device is removed from the injection site, the needle guard 540 returns to its original position under the force of return spring 660, concealing the injecting needle 480. The locking ring 700 locks the needle guard 540 in place to prevent re-exposure of the injecting needle 480. Alternatively, a push button could be located at the proximal end of the device and be locked in an idle position. The movement of the needle guard 540 could unlock the push button and allow the user to depress it and consequently fire the device.

Figure 20B:
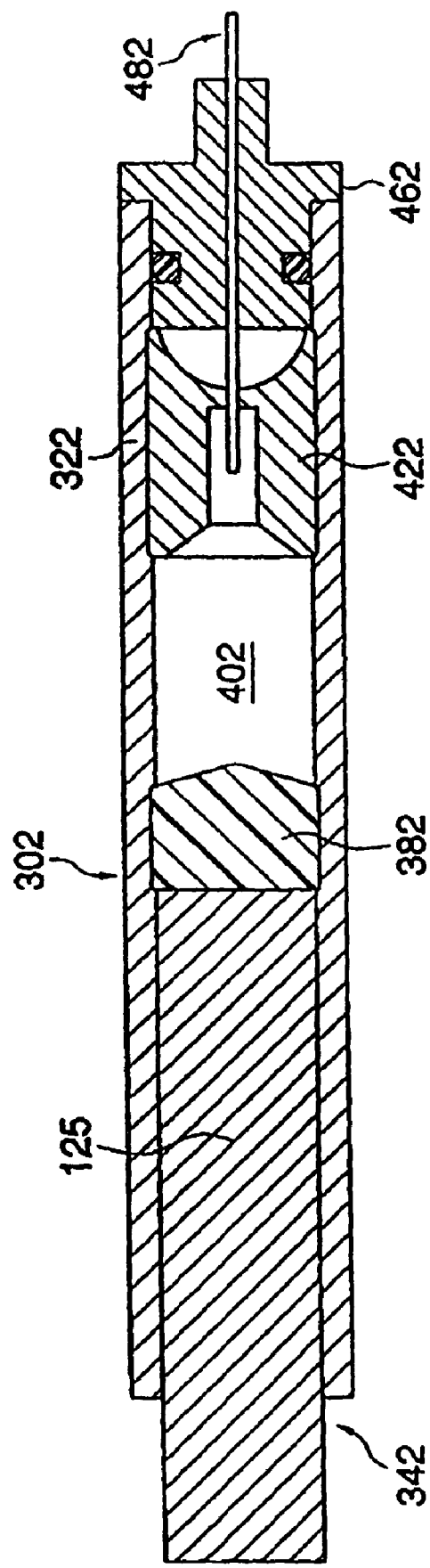
FIG. 20b is a cross-sectional view of an alternative embodiment of the cartridge assembly of FIGS. 14a and 14b.

FIG. 20b shows another embodiment of the cartridge assembly 302 of the preferred embodiment. The cartridge assembly 302 comprises a glass ampule 322 and a needle assembly 462 sealed on its distal end. A pierceable seal 422 is located in proximity to the proximal end of the injecting needle 482 and creates a barrier between the medicament 402 and the injecting needle 482. A rubber stopper 382 is slideable within the glass ampule 322 and seals an opening 342 in its proximal end so the medicament 402 stays inside the glass ampule 322. Upon firing of the injector, the ram 125 urges the rubber stopper 382 toward the distal end of the injector. Since the medicament 402 is an incompressible fluid, the pierceable seal 422 is forced onto the distal end of the injecting needle 482, thereby breaking the barrier and creating the drug path. With this cartridge assembly 302, no turning of the device is required to create the drug path, and the threads on the inner housing 25 and on the needle holder 260 can be replaced by known permanent fixing techniques, such as gluing or welding.

Figure 27:
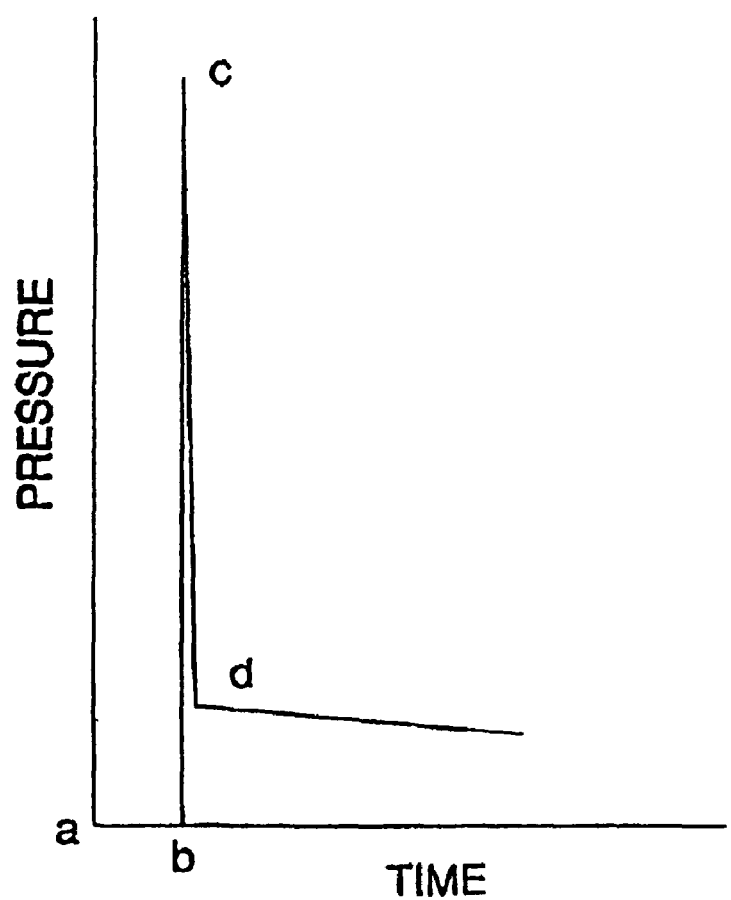
FIG. 27 is a schematic expressing a pressure-time curve for a jet injector.

A significant advantage of the needle assisted jet injector according to the present invention is that it allows for a lower pressure to deliver the medicament at the desired rate. In this regard, administering an injection using either a fixed or retractable needle requires less energy and force than conventional jet injector devices. FIG. 27 shows a pressure-time curve for a jet injector. The peak pressure at point c is the pressure needed to penetrate the skin and point d and beyond is the pressure at which a jet stream of medicament is delivered. As shown in the chart below, needle assisted jet injectors do not need to achieve as high as peak pressure as conventional jet injectors because the outer layer of skin is penetrated by the needle.

| Pressure and Time (sec.) to Inject 1 cc | | |
|---|---|---|
| Pressure | 26 Gauge needle | 27 Gauge needle |
| 150 psi | 2.1 | 4.2 |
| 200 psi | 1.9 | 3.9 |
| 240 psi | 1.7 | 3.3 |
| 375 psi | 1.4 | 3.1 |

A lower peak pressure can be used to deliver the medicament to the desired region and still achieve a short injection time. It is also possible that a lower steady state pressure can be used to deliver the jet stream after the needle and the jet injection have reached the desired region.

Reduced operating pressure decreases the chances of glass ampule breakage. The chart below shows the statistical predictions of breakage for glass cartridges at different pressures, based on the Gaussian distribution of actual breakage rates at various pressures.

| Breakage Rates for Glass Cartridges | |
|---|---|
| Pressure (psi) | Breakage Rate |
| 310 | $1.5 \times 10^{-11}$ |
| 412 | $1.0 \times 10^{-9}$ |

It can be seen that a relatively small increase in pressure (100 p.s.i. (689 kPa)) increases the breakage rate by two orders of magnitude. Thus, the reduced operating pressure of the needle assisted injection device of the present invention greatly reduces the risk of ampule breakage.

Experimentation has confirmed that the needle assisted injector according to the present invention can be operated using a lower generating energy source and still maintain the quality of the injection. Specifically, experimentation has shown that a higher percentage of successful injections can be achieved with a needle assisted jet injector having a needle that penetrates the skin to a depth of 1 mm and 20 lb. (89 N) force generating means as with a conventional needleless jet injectors having 55 lb. (2445 N) force generating means. Similar results have been achieved with needles that penetrate 1-3 mm and force generating sources providing 20 lbs. and 40 lbs. (89 to 178 N) of force.

Another advantage of the needle assisted jet injector according to the present invention, shown in the chart below, is the decreased injection time compared to syringes or auto-injectors.

| Comparison of Operating Properties for Injection Devices | | | | |
|---|---|---|---|---|
| | Spring Force (Lbf.) | Dia. Of Fluid Chamber (inches) | Avg. Pressure (psi) | Volume of Injection (ml) | Injection Time (sec) |
| Jet Injector | 110 | 0.233 | 2111 | 0.5 | 0.165 |
| $1^{st}$ Needle Assisted Injector | 30 | 0.352 | 227 | 0.5 | <1 |
| $2^{nd}$ Needle Assisted Injector | 15 | 0.231 | 233 | 0.5 | <1 |
| Conventional Syringe | N/A | 0.351 | 5 | 0.5 | 3-5 |

As previously discussed, auto-injectors and syringes have injection times of several seconds or more. During this injection time, the quality of the injection can be compromised due to any number of factors. For example, the patient could move the syringe or auto-injector prior to completion of the injection. Such movement could occur either accidentally or intentionally because of injection-related pain. In contrast, the needle assisted jet injector, like other jet injectors, can have an injection time of less than 1 second. The short injection time minimizes the possibility of compromising the quality of the injection.

While it is apparent that the illustrative embodiments of the invention herein disclosed fulfill the objectives stated above, it will be appreciated that numerous modifications and other embodiments may be devised by those skilled in the art. Therefore, it will be understood that the appended claims are intended to cover all such modifications and embodiments which come within the spirit and scope of the present invention.

What is claimed is:

1. A jet injection device, comprising:
    a housing member having distal and proximal ends;
    a fluid chamber within the housing member holding about between 0.02 ml and 3 ml of a medicament comprising fluid;
    an injection-assisting needle disposed at the distal end of the housing member, having an injecting end, and having an association with the fluid chamber to provide a fluid pathway from the fluid chamber through the needle, the injecting end of the injection-assisting needle having an axial opening for ejection of the medicament;
    a plunger movable within the fluid chamber; and
    a force generating mechanical member within the housing member that is elastically-deformed so as to provide sufficient force to eject the medicament from the fluid chamber through the needle by jet injection in a high-speed jet that exits the injecting end of the needle through the axial opening thereof at a fluid pressure of about between 100 and 1000 p.s.i. to penetrate patient tissue to a distance through and axially beyond the insertion point to an injection site;
    wherein the injecting end of the needle has a position extending from the housing member by a length selected for inserting into a patient such that the injecting end reaches a needle insertion point at a depth of up to about 5 mm below the surface of the patient's skin; and
    wherein the device is further configured such that activation of the force generating mechanical member applies the generated force to the plunger to expel the medicament from the fluid chamber.

2. The jet injection device of claim 1, wherein the injection site is subcutaneous.

3. The jet injection device of claim 1, wherein the needle insertion point is at a depth of between about 1 mm and 5 mm.

4. The jet injection device of claim 1, wherein the needle insertion point is at a depth of up to about 3 mm.

5. The jet injection device of claim 1, wherein the force generating source and needle are configured such that the medicament is injected at a rate of at least 0.40 ml/sec upon activation of the force generating source.

6. The jet injection device of claim 1, wherein the force generating source and needle are configured to inject the amount of the medicament to the injection site in less than about 2.75 seconds.

7. The jet injection device of claim 1, wherein the force generating source and needle are configured to inject the medicament at a rate so that about 1 ml of the medicament is ejected in about 2 seconds.

8. The jet injection device of claim 1, wherein the force generating source and needle are configured to apply to the medicament a pressure that reaches up to about 500 p.s.i.

9. The jet injection device of claim 8, wherein the force generating source and needle are configured to apply to the medicament a pressure that reaches between about 150 and 375 p.s.i.

10. The jet injection device of claim 1, wherein the axial opening of the needle injecting end has a diameter of about between 0.004 to 0.012 inches and the needle has a length sufficient for penetrating the skin to a depth of between about 1 mm and 5 mm.

11. The jet injection device of claim 1, wherein the needle is a 26 to 27 gage needle.

12. The jet injection device of claim 1, wherein the needle further comprises a proximal portion that has common axial cross-sectional dimensions with the injecting end and extends proximally into an injection device housing member in which the fluid chamber is disposed during the ejection of the medicament, the proximal portion being longer than the injecting end.

13. The jet injection device of claim 12, wherein the proximal portion and injecting end have substantially common and continuous inner and outer diameters.

14. The jet injection device of claim 1, wherein the fluid chamber is made of glass.

15. The jet injection device of claim 1, wherein the housing member has a concealing association with the needle, wherein the device is configured such that the needle injecting end is extendable from the housing member to allow the insertion to the needle insertion point.

16. The jet injection device of claim 15, wherein the housing member comprises a needle shield located at the distal end of the housing member for concealing the needle, the needle shield being moveable between: a protecting position, in which the needle is disposed within the guard prior to activation, and an injecting position, in which the tip of the needle is exposed for insertion to the insertion point.

17. The jet injection device of claim 16, further comprising an activation element operatively associated with the shield such that the activation element activates the force generating source upon retraction of the shield from the protecting position to the injection position.

18. The jet injection device of claim 1, further comprising a retraction element configured for retracting the needle into the housing member after the medicament is ejected.

19. The jet injection device of claim 1, wherein the housing member and needle are cooperatively associated to allow the insertion of the needle to the insertion point.

20. A jet injection device, comprising:
a housing member having distal and proximal ends;
a fluid chamber within the housing member for holding at least about 0.02 ml to 3 ml of a medicament;
an injection-assisting needle disposed at the distal end of the housing member, having an injecting end, and having an association with the fluid chamber to provide a fluid pathway from the fluid chamber through the needle, the injecting end of the injection-assisting needle having an axial opening for ejection of the medicament;
a plunger movable within the fluid chamber; and
a force generating source comprising a spring pre-compressed to provide sufficient force to eject the medicament from the fluid chamber through the needle by jet injection in a high-speed jet that exits the injecting end of the needle through the axial opening thereof at a pressure of about between 100 and 1000 p.s.i. so as to penetrate patient tissue to a distance through and axially beyond the insertion point to an injection site wherein the needle insertion point is located more superficially than the injection site;
wherein the injecting end of the needle has a position extending from the housing member by a length selected for inserting into a patient such that the injecting end reaches a needle insertion point at a depth of no more than about 5 mm below the surface of the patient's skin; and
wherein the force generating source is further configured such that activation of the force generating source applies the force of the pre-compressed spring to the plunger to expel the medicament from the fluid chamber.

21. The jet injection device of claim 1 wherein the fluid chamber comprises a frangible material and the force generating member comprises a pre-compressed spring.

22. The jet injection device of claim 1 wherein the fluid chamber comprises glass and the force generating member comprises a pre-compressed elastomer.

* * * * *